(12) United States Patent
Hyers et al.

(10) Patent No.: US 7,758,896 B2
(45) Date of Patent: Jul. 20, 2010

(54) POROUS CALCIUM PHOSPHATE NETWORKS FOR SYNTHETIC BONE MATERIAL

(75) Inventors: Robert Hyers, Amherst, MA (US); Michael SanSoucie, Turners Falls, MA (US)

(73) Assignee: University of Massachusetts, Boston, MA (US)

(*) Notice: Subject to any disclaimer, the term of this patent is extended or adjusted under 35 U.S.C. 154(b) by 934 days.

(21) Appl. No.: 11/107,066

(22) Filed: Apr. 15, 2005

(65) Prior Publication Data

US 2005/0255159 A1     Nov. 17, 2005

Related U.S. Application Data

(60) Provisional application No. 60/562,769, filed on Apr. 16, 2004.

(51) Int. Cl.
*A61K 33/42* (2006.01)
*A61F 2/28* (2006.01)

(52) U.S. Cl. .................. 424/602; 424/423; 424/484; 623/23.56; 623/23.61

(58) Field of Classification Search .............. 424/602, 424/423, 484
See application file for complete search history.

(56) References Cited

U.S. PATENT DOCUMENTS

| | | | |
|---|---|---|---|
| 3,149,081 A * | 9/1964 | Bowman et al. ............ 502/210 |
| 3,905,047 A * | 9/1975 | Long ..................... 623/23.56 |
| 5,626,861 A | 5/1997 | Laurencin et al. |
| 5,847,012 A | 12/1998 | Shalaby et al. |
| 6,201,039 B1 | 3/2001 | Brown et al. |
| 6,214,368 B1 | 4/2001 | Lee et al. |
| 6,306,424 B1 | 10/2001 | Vyakarnam et al. |
| 6,376,573 B1 | 4/2002 | White et al. |
| 6,471,993 B1 | 10/2002 | Shastri et al. |
| 6,508,838 B2 | 1/2003 | Lee et al. |
| 6,582,672 B1 | 6/2003 | Bonfield et al. |
| 6,585,946 B1 | 7/2003 | Bonfield et al. |
| 6,585,992 B2 | 7/2003 | Pugh et al. |
| 6,596,338 B2 | 7/2003 | Scott et al. |
| 6,605,293 B1 | 8/2003 | Giordano et al. |
| 6,749,639 B2 | 6/2004 | Lewallen |
| 6,823,871 B2 | 11/2004 | Schmieding |
| 6,840,961 B2 | 1/2005 | Tofighi et al. |
| 6,846,493 B2 | 1/2005 | Pugh et al. |
| 6,949,251 B2 | 9/2005 | Dalal et al. |
| 6,953,594 B2 | 10/2005 | Lee et al. |
| 6,955,716 B2 | 10/2005 | Xu et al. |
| 7,005,136 B2 | 2/2006 | Nathan et al. |
| 7,037,867 B2 | 5/2006 | Yu et al. |
| 7,045,105 B2 | 5/2006 | Lagow |
| 7,052,710 B2 | 5/2006 | Giordano et al. |
| 7,066,962 B2 | 6/2006 | Swords |
| 7,078,221 B2 | 7/2006 | Oppermann et al. |
| 7,112,417 B2 | 9/2006 | Vyakarnam et al. |
| 7,122,057 B2 | 10/2006 | Beam et al. |
| 7,172,629 B2 | 2/2007 | McKay |
| 7,186,267 B2 | 3/2007 | Aston et al. |
| 2002/0049405 A1 | 4/2002 | Deslauriers |
| 2003/0009235 A1 | 1/2003 | Manrique et al. |
| 2003/0023305 A1 | 1/2003 | McKay |
| 2003/0050710 A1 | 3/2003 | Petersen et al. |
| 2003/0055511 A1 | 3/2003 | Schryver et al. |
| 2003/0055512 A1 | 3/2003 | Genin et al. |
| 2003/0064090 A1 | 4/2003 | Khouri et al. |
| 2003/0069638 A1 | 4/2003 | Barlow et al. |
| 2003/0099630 A1 | 5/2003 | DiBenedetto et al. |
| 2003/0152606 A1 | 8/2003 | Gerber |
| 2003/0180344 A1 | 9/2003 | Wise et al. |
| 2003/0217415 A1 | 11/2003 | Crouch et al. |
| 2003/0219466 A1 | 11/2003 | Kumta et al. |
| 2003/0232071 A1 | 12/2003 | Gower et al. |
| 2003/0235621 A1 | 12/2003 | Miller et al. |
| 2004/0002759 A1 | 1/2004 | Ferree |
| 2004/0002770 A1 | 1/2004 | King et al. |
| 2004/0019132 A1 | 1/2004 | Long et al. |
| 2004/0024081 A1 | 2/2004 | Trieu et al. |

OTHER PUBLICATIONS

Hasegawa, A thermochemical study of the CaO-P2O5-FeO system-the region in equilibrium with solid Ca3P2O8, Current Advances in Materials and Processes-ISIJ (1999), vol. 12, No. 4, p. 817.*
Levin et al., Phase Diagrams for Ceramists, The American Ceramic Society (1964), pp. 4-8, 14-25, 29-31, 208, 214, 216, 223, 569-574, 596.*
HCAPLUS abstract 2008:8130 (2008).*
Barralet, JE; Grover, L; Gaunt, T; Wright, AJ; and Gibson, IR; Preparation of Macroporous Calcium Phosphate Cement Tissue Engineering Scaffold; Biomaterials; 2002, 3063-3072, vol. 23.
Bignon, A; Chouteau, J; Chevalier,J; Fantozzi, G; Carret, JP; Chavassieux, P; Boivin, G; Melin, M; and Hartmann,D; Effect of Micro- and Macroporosity of Bone Substitutes on Their Mechanical Properties and Cellular Response; Journal of materials Science: Materials in Medicine, Dec. 2003, 1089-1097, vol. 14, No. 12.
Quinn, JB; Chow, LC; Takagi, S.; and Xu, HH; Fast-Setting Calcium Phosphate Scaffolds with Tailored Macropore Formation Rates for Bone Regeneration; Journal of Biomedical Materials Research Part A, 2004, 725-734, vol. 68A, No. 4.
Filmon, R; Retailleau-Gaborit, N; Grizon, F; Galloyer, M; Cincu, C; Basle, MF; and Chappard, D; Non-Connected Versus Interconnected Macroporosity in Poly(2-hydroxyethyl Methacrylate) Polymers. An X-ray Microtomographic and Histomorphometric Study; J. Biomater Sci. Polym. Ed., 2002, 1105-1117; vol. 13, No. 10.

(Continued)

*Primary Examiner*—John Pak
(74) *Attorney, Agent, or Firm*—Reinhart Boerner Van Deuren s.c.

(57) ABSTRACT

A porous composition comprising a hydroxyapatite material, as can be made from a mixture of calcium phosphate, calcium oxide and a removable inorganic porogen. In other embodiments, the present invention provides a method of making such a porous hydroxyapatite material or using a ternary system to prepare a two-phase composition enroute to a biomimetic bone material.

21 Claims, 17 Drawing Sheets

OTHER PUBLICATIONS

Harrop, JS; and Przybylski, GJ; Use of an Osteoconductive Agent (Norian) in Anterior Surgical Management of Odontoid Fractures; Neurosurg Focus, 2000, vol. 8, No. 6.

Berger, G; Gildenhaar, R; and Ploska, U; Rapid Resorbable, Glassy Crystalline Materials on the Basis of Calcium Alkali Orthophosphates, Biomaterials, Nov. 1995, 1241-1248, vol. 16, No. 16.

Truumees, E; and Herkowitz, HN; Alternatives to Autologous Bone Harvest in Spine Surgery; The University of Pennsylvania Orthopaedic Journal; 1999, 77-88, vol. 12.

Tadic, D; Beckmann, F; Schwarz, K; and Epple, M; A Novel Method to Produce Hydroxyapatite Objects with Interconnecting Porosity that Avoids Sintering; Biomaterials, 2004, 3335-3340, vol. 25.

Thomson, RC; Yaszemski, MJ; Powers, JM; and Mikos, AG; Hydroxyapatite Fiber Reinforced Poly(alpha-hydroxy ester) Foams for Bone Regeneration; Biomaterials, Nov. 1998, 1935-1943; vol. 19, No. 21.

Vogt, S; Larcher, Y; Beer, B; Wilke, I; and Schnabelrauch, M; Fabrication of Highly Porous Scaffold Materials Based on Functionalized Oligolactides and Preliminary Results on Their Use in Bone Tissue Engineering; European Cells and Materials, 2002, 30-38, vol. 4.

Shastri, VP; Martin, I; and Langer, R; Macroporous Polymer Foams by Hydrocarbon Templating; PNAS, Feb. 29, 2000, 1970-1975, vol. 97, No. 5.

Sachlos, E; and Czernuszka, JT; Making Tissue Engineering Scaffolds Work. Review on the Application of Solid Freeform Fabrication Technology to the Production of Tissue Engineering Scaffolds; European Cells and Materials, 2003, 29-40, vol. 5.

Guldberg, RE; Ballock, RT; Boyan, BD; Duvall; CL; Lin, ASP; Nagaraja, S; Oest, M; Phillips, J; Porter, BD; Robertson, G; and Taylor; WR; Analyzing Bone, Blood Vessels, and Biomaterials with Microcomputed Tomography; IEEE Engineering in Medicine and Biology Magazine, Sep./Oct. 2003, 77-83, vol. 22, No. 5.

Grant, M and Elder, KR; Spinodal Decomposition in Fluids; Physical Review Letters, Jan. 4, 1999, 14-16, vol. 82, No. 1, American Physical Society.

Nam, YS; and Park, TG; Porous Biodegradable Polymeric Scaffolds Prepared by Thermally Induced Phase Separation; Journal of Biomedical Materials Research, 1999, 8-17, vol. 47, No. 1, Willey Interscience.

Murphy, WLl; Dennis, RG; Kileny, JL; and Mooney, David J; Salt Fusion: An Approach to Improve Pore Interconnectivity Within Tissue Engineering Scaffolds; Tissue Engineering, 2002, 43-52, vol. 8, No. 1.

Katti, K; and Gujjula, P; Control of Mechanical Responses in Insitu Polymer-Hydroxyapatite Composites for Bone Replacement; 15th ASCE Engineering Mechanics Conference, Jun. 2-5, 2002, Columbia University, New York, NY.

Sutter, B; Ming, DW; Clearfield, A; and Hossner, LR; Mineralogical and Chemical Characterization of Iron-, Manganese-, and Copper-Containing Synthetic Hydroxyapatites; Soil Sci. Soc. Am. J., Nov.-Dec. 2003, 1935-1942, vol. 67.

Golden, DC; and Ming, DW; Nutrient-Substituted Hydroxyapatites: Synthesis and Characterization; Soil Sci. Soc. Am. J. 1999, 657-664, vol. 63.

Gross, KA; Jackson, R; Cashion, JD; and Rodriguez-Lorenzo, LM; Iron Substituted Apatites: A Resorbable Biomaterial with Potential Magnetic Properties; European Cells and Materials, 2002, 114-117, Suppl. 2, vol. 3.

Deisinger, U; Stenzel, F; and Ziegler, G; Development of Hydroxyapatite Ceramics with Tailored Pore Structure; Key Engineering Materials, 2004, 977-980, vols. 254-256, Trans Tech Publications, Ltd., Switzerland.

Mikos, AG; and Temenoff, JS; Formation of Highly Porous Biodegradable Scaffolds for Tissue Engineering; Electronic Journal of Biotechnology, Aug. 15, 2000, 114-119, vol. 3, No. 2.

Adolfsson, E; Macro Porous Hydroxyapatite with Designed Pores; Key Engineering Materials, 2004, 1025-1028, vols. 254-256, Trans Tech Publications Ltd., Switzerland.

Simsek, FA; Chemical Preparation of Calcium Hydroxyapatite Bioceramic Powders in Synthetic Body Fluids at 37° C (pH-7.4) and Its Use in (in Situ) Coating of Ti-6Al-4V and Stainless Steel (316L) Surfaces; Thesis, Middle East Technical University, Ankara,Turkey, Jul. 1997.

Calderin, L; and Stott, MJ; Electronic and Crystallographic Structure of Apatites; Physical Review B, 2003, 134106-1-134016-7, vol. 67, American Physical Society.

Sinha, A; Ingle, A; Munim, KR; Vaidya, SN; Sharma, BP; and Bhisey, AN; Development of Calcium Phosphate Based Bioceramics; Bull. Mater. Sci., Dec. 2001, 653-657, vol. 24, No. 6.

Barroug, A; Kuhn, L; and Glimcher, MJ; Controlled Adsorption and Release of Calcium Phosphates for Drug Delivery Applications; The 3rd International Hydroxyapatite Conference, Jun. 3-5, 2003, Lisbon.

Shi, D; Jiang, G; and Wen, X; in Vitro Behavior of Hydroxyapatite Prepared by a Thermal Deposition Method; Processing and Fabrication of Advanced Materials VIII, Singapore, Sep. 8-10, 1999, pub. 2001, World Scientific, p. 117.

Gross, K; Hydroxyapatite—Synthesis of Hydroxyapatite Powders; http://www.azom.com/details. asp?ArticleID=1519 (last visted Jun. 4, 2007).

Hench, LL; Bioceramics; J. Am. Ceram. Soc., 1998, 1705-1728, vol. 81, No. 7.

Schwarz, JA; Current Projects, http://www.ecs.syr.edu/faculty/schwarz/projectl.htm (last visited Jun. 4, 2007).

A Biocompatible Polymer p(HEMA), http://www.med.univ-angersiddiscipline/lab_histo/page_phemaAngl.htm (last visited Jun. 4, 2007).

SanSoucie, M; Porous Hydroxyapatite Networks for Synthetic Bone Material By Spinodal Decomposition; M.S. Thesis, May 2004, University of Massachusetts Amherst.

SanSoucie et al. Calcium Phosphate Based Ceramics via Sinodal Decomposition, Bioceramics, Materials and Applications V (May 2005), pp. 111-117.

Foster, Contribution to the Interpretation of Phase Diagrams by Ceramists, Journal of the American Ceramic Society, May 1951, vol. 34, No. 5, pp. 151-160.

Bloc et al., Structural Interpration of Immiscibility in Oxide Systems;I, Analysis and Calculation of Immiscibility, Journal of the American Ceramic Society, Mar. 1957, vol. 40, No. 3, pp. 95-106.

Block et al., Structural Interpretation of Immiscibility in Oxide Systems:II, Coordination Principles Applied to Immiscibility, Journal of the American Ceramic Society, Apr. 1957, vol. 40, pp. 113-118.

Malysheva, AY; and Beletskii, BI; Biocompatibility of Apatite-Containing Implant Materials; Inorganic Materials, 2001, 180-183, vol. 37, No. 2.

Berger, G; Gildenhaar, R; Ploska, U.; and Willfahrt, M; Syntheses of Rapidly Resorbable Calcium Phosphate Ceramics with High Macro or High Micro Porosity; Bioceramics, 367-370, vol. 10. (Proceedings of the 10th International Symposium on Ceramics in Medicine, Paris, France, Oct. 1997).

SanSoucie, M; and Hyers, RW; Calcium Phosphate Based Ceramics Via Spinodal Decomposition; Bioceramics: Materials and Applications V, 111-117, The American Cancer Society.

Yang, S; Leong, KF; Du, Z; and Chua, CK; The Design of Scaffolds for Use in Tissue Engineering. Part I. Traditional Factors; Tissue Engineering, 2001, 679-689, vol. 7, No. 6.

Pompe, W; Worch, H; Epple, M; Friess, W; Gelinsky, M; Greil, P; Hempel, U; Scharnweber, D; and Schulte, K; Functionality Graded Materials for Biomedical Applications; Materials Science and Engineering, 2003, 40-60, vol. 362, Nos. 1-2.

Vaccaro, AR; The Role of the Osteoconductive Scaffold in Synthetic Bone Graft; Orthopedica; May 2002, 571-578, vol. 25, No. 5.

* cited by examiner

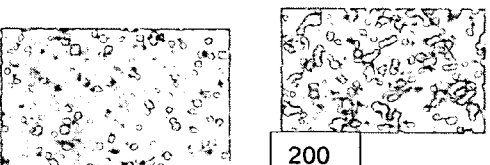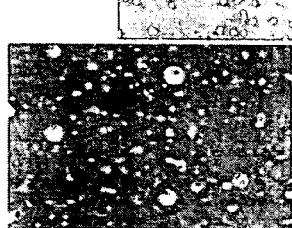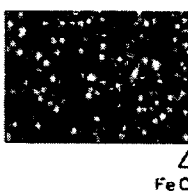
Figure 7B
Figure 7C
Figure 7D
Figure 7A
Figure 7E
Figure 7F
Figure 7G   Figure 7H   Figure 7I   Figure 7J

POROUS CALCIUM PHOSPHATE NETWORKS FOR SYNTHETIC BONE MATERIAL

This application claims priority benefit of U.S. application Ser. No. 60/562,769, filed Apr. 16, 2004, the entirety of which is incorporated herein by reference.

BACKGROUND OF THE INVENTION

Bone grafts are used to provide anatomic mechanical replacement of bone lost due to trauma or removal of cancerous tissue. The source of human bone graft material is primarily limited to the patient's own skeleton (autogenous) or a limited supply of donated bones (allogenous) maintained in bone banks. There is a need for a suitable synthetic source of compatible bone graft material.

Bone is the second most implanted material in humans after blood. There are over 450,000 bone grafts in the United States and over 2.2 million worldwide. Autogenous bone used as an autograft is superior to allogeneic bone, but has the disadvantages of donor site morbidity, prolonged surgery time and limitations in quantity of graft available (especially when large, load bearing cortical segments are required). Collection of the needed material increases the surgical anesthetic time, risk of infection, and intra-operative blood loss. Sufficient quantities and dimensions may not be available or may require multiple donor sites; and damage at the donor site may result in unacceptable patient morbidity. In addition, the quality of the material may be poor if it is necessary to harvest additional bone from a previously used autograft site. In part due to these restrictions, bone allografts are used extensively in human surgery, accounting for the materials used in vast majority of bone grafts.

The primary source of bone allograft material is bone banks. Bone banking was pioneered by the military in the Korean War period due to the need for bone grafts in reconstructive surgery after trauma. The American Association of Tissue Banks (www.aatb.org) was established in 1976 as a not-for-profit, peer group organization to facilitate the provision of tissue on a national basis. AATB publishes standards and technical manuals for collection, processing, storage, and distribution of tissue, and accredits tissue banks as complying with these standards. The majority of available bone allograft material in the United States is obtained and maintained by the limited number (about 60) of AATB approved bone banks.

However, the availability of bone bank material is limited by the possibility of the transmission of infectious diseases, notably HIV/AIDS and hepatitis B and C. The U.S. Food and Drug Administration regulates both the screening of domestic bone bank material and the importation of foreign tissue, for which there may not be proper information on source and donor health. The number of domestic organ donors has been relatively constant at about 5,000-6,000 cadaveric donors per year. At present, the number of patients waiting for donated organs and tissue far exceeds the number of donors each year.

Another option is the xenograft, which is a living or non-living transplant from another species. Non-living, chemically treated xenografts are regularly used as heart valve replacements. Bovine bone grafts are seldom used due to concerns over transmission of viruses and prions (e.g., bovine spongiform encephalitis, "mad cow disease"). Hydroxyapatite derived from marine coral is also considered a xenograft. However, harvesting marine coral is limited by an international treaty. An implant of synthetic bone would avoid the problems inherent in traditional autografts, allografts, and xenografts, but only if the synthetic bone graft material was physically, chemically and functionally compatible with natural bone.

Human bone mass, and thus bone density, and strength decreases with age (osteoporosis), making bones particularly susceptible to fracture in older people. Bone mass decreases because the bone-growing cells (osteoblasts) become less productive at making new bone and repairing microfractures. Fractured hips and collapsed vertebrae are a common result of low bone density in older people. A comparison between normal bone and osteoporotic bone is shown in FIG. 1. FIGS. 1A and 1B show a comparison of photomicrographs between normal bone and osteoporotic bone. FIG. 1A shows a photomicrograph of normal cancellous bone of a 30 year old woman and FIG. 1B shows a photomicrograph of osteoporotic cancellous bone from a 60 year old woman, whether the mineral appears as dark areas, and pores appear as light areas.

Natural bone consists mainly of minerals and collagen fibers, with approximately 69% by weight being hydroxyapatite (HAp, $Ca_{10}(PO_4)_6(OH)_2$). In practice, the chemical composition of bone mineral is a bit more complex than this formula suggests. The calcium sites are doped to about 1.5% with several mono- or divalent cations (Na, K, Mg, Zn, Fe, Sr, Pb, Ba, Cu, etc.). The hydroxyl and phosphate groups are doped with carbonate ions to about 5% by weight, and the mineral has lower oxygen content. Bone mineral has the generic formula of $Ca_{8.3}(PO_4)_{4.3}(HPO_4,CO_3)_{1.7}(OH,CO_3)_{0.3}$.

Mature bone is either cortical bone or cancellous bone. Cortical bone, which is also known as compact bone, is always on the exterior surrounding the cancellous bone. Cancellous bone, also known as trabecular or spongy bone, develops near the ends of long bones, at the interior of small bones, and between the surfaces of flat bones. Cortical bone consists of several irregular cylindrical units, called Haversian systems or secondary osteons, each consisting of a central Haversian canal containing a neurovascular bundle surrounded by concentric lamellae of bony tissue. The Haversian canals average about 50 μm in diameter, with those closer to the marrow cavity being slightly larger. Within each cavity are one or two capillaries and usually some nerve fibers. Cancellous bone consists of an array of plates and rods of bone tissue ("trabeculae") and forms an open-celled foam. The trabeculae represent "unrolled" osteons. The difference between compact and spongy bone is the amount of solid matter and the size, shape, and number of spaces in each. In compact bone, the spaces are small and the solid matter is extensive, while the opposite is true in spongy bone.

Synthetic bone is typically made from hydroxyapatite or a combination of hydroxyapatite and tricalcium phosphate ($Ca_3(PO_4)_2$). These materials can be made with a porous structure, which allows natural bone to grow into the pores and form a good bond. Current methods for the production of hydroxyapatite typically involve sintering at high temperatures. However HAp decomposes at the sintering temperatures, approximately 1000° degrees Celsius. Sintering at lower temperatures produces weak bonds, while sintering at higher temperatures causes low porosity and poor phase purity (due to decomposition). This makes sintering an inadequate method for producing good quality HAp implant material for structural bone replacement.

An ideal synthetic bone graft material would be resorbable so it will be gradually broken down and replaced with new natural bone continuously through normal bone remodeling. The material should be porous and osteoconductive to be populated by bone cells. The physical properties of the synthetic bone graft material should be compatible with natural bone to provide mechanical support while participating in the proper transmission of local stress required by the endogenous control mechanism of bone remodeling and bone growth.

A disadvantage of using metals and nonresorbable ceramics as bone implants based on the phenomenon of stress shielding, which was discovered by Julius Wolff in 1892. Materials implanted into bone will the load that the bone would normally experience. The stress that the natural bone is subjected to is based on the ratio of the elastic modulus of the implant material to that of the natural bone. If the elastic modulus of the implant material is much higher than the elastic modulus of the natural bone, the bone will experience proportionally lower stresses. This will cause the bone to adapt to this lower stress by atrophy. The elastic modulus of several materials, including cortical bone, is listed in Table 1. Most nonresorbable materials have a higher elastic modulus than bone, and thus are a poor choice for synthetic bone graft materials.

TABLE 1

Mechanical properties of Bone and Selected materials

| Material | Density (g/ml) | Elastic Modulus (GPa) | Modulus/Density |
|---|---|---|---|
| Graphite Fiber | 1.8 | 276 | 153.3 |
| Alumina | 3.9 | 345 | 88.5 |
| Hydroxyapatite | 3.2 | 279 | 87.2 |
| Hardwoods | 1.3 | 100 | 76.9 |
| Ivory | 1.9 | 90 | 47.4 |
| Quartz | 2.65 | 103 | 38.9 |
| Aluminum | 2.7 | 70 | 25.9 |
| Stainless Steel | 8.02 | 193 | 24.1 |
| Titanium | 5.0 | 114 | 22.8 |
| Zirconium | 6.5 | 83 | 12.8 |
| PMMA (solid) | 1.18 | 3 | 2.5 |
| UHMW PE | 0.94 | 1 | 1.1 |
| Compact Bone | 2.1 | 20 | 9.5 |
| Trabecular Bone | 1.0 | 0.1 | 0.1 |

The combination of hard inorganic and flexible organic components gives natural bone tissue nearly equal resistance to compression and tension. Bone is comparable to cast iron in tensile strength, with only a third of the weight. The breaking stress of bone and cast iron are 235 and 273 MPa, respectively.

A porous biomaterial allows natural bone to grow into the implant. Porosity allows entry by osteoclasts and osteoblasts which leads to osteointegration and vascularization. It has been shown that 37% of pore volumes must be enclosed by interconnections greater than 100 μm for mineralized bone in growth. Larger pores and more interconnectivity would produce more rapid and complete ingrowth; however, a tradeoff between ingrowth and implant strength must be achieved as larger pores greatly decrease the strength of the implant.

Ceramics used for the repair, reconstruction, and replacement of diseased or damaged parts of the body are termed bioceramics. Bioceramics can be designed to be very similar in chemistry and structure to natural bone. Bioceramics can be classified into four categories: nearly inert bioceramics, such as alumina and carbon; surface-active bioceramics, such as Bioglass; resorbable bioceramics, such as calcium sulfate and tricalcium phosphate and composites, such as polymer-ceramic composites and HAp/TCP mixtures. See, generally, Vincenzini, P., ed., *High Tech Ceramics* (*Materials Science Monographs*, 38A), Elsevier, Amsterdam, 1987. Much work on synthetic bone graft materials has been on Bioglass and other glass-ceramic composites, polymer-ceramic composites and HAp/TCP calcium phosphate mixtures.

Bioglass, developed by Hench and co-workers in the early 1970s, is a glass designed to bond directly to bone by providing surface reactive silica, calcium, and phosphate groups in an alkaline pH environment. Bioglass 45S5 contains 45 wt % $SiO_2$, 24.5 wt % CaO, 24.5 wt % $Na_2O$, and 6 wt % $P_2O_5$. However, the orthopedic applications of Bioglass are limited due to the slow kinetics of surface reaction rates and the corresponding slow development of interfacial bond strength. Bioglass also has mechanical properties common to other glass-ceramic composites: low tensile strength, ductility, and modulus mismatch with natural bone.

The most widely used bioceramics are hydroxyapatite (HAp, $Ca_{10}(PO_4)_6(OH)_2$) and tricalcium phosphate (TCP, $Ca_3(PO_4)_2$). Calcium phosphate materials have several advantageous characteristics including a lack of local or system toxicity, a lack of inflammatory or foreign body response, an absence of intervening fibrous tissue between implant and bone, and the ability to become directly bonded to bone.

TCP has been shown to resorb rather quickly, but HAp is the more similar to biological apatite crystals in chemistry and physical properties. Hydroxyapatite dissolves much more slowly than TCP in a variety of fluids. It has been shown that when dense HAp and TCP of similar purity and microstructure were compared, the TCP dissolved 12.3 times faster in acid solutions and 22.3 times faster in basic solutions.

A combination of fast resorbing TCP and much stronger Hap, as can be termed biphasic calcium phosphate (BCP), provides a combination of desirable properties. See Legeros, R., et al., "Biphasic calcium phosphate bioceramics: preparation, properties and applications," Journal of Materials Science: Materials in Medicine, vol. 14, no. 3, 2003, pp. 201-209. BCP mixtures have been studied as bone substitute materials for dental and orthopedic applications (Daculsi, G., et al., Macroporous calcium phosphate ceramic for long bone surgery in humans and dogs. Clinical and histological study, *J. Biomedical Materials Research,* 24 1990, 379-396).

Biphasic calcium phosphates are a mixture of HAp and beta-TCP. The bioactivity of biphasic calcium phosphate ceramics can be controlled by altering the HAp/beta-TCP ratio. The dissolution rate of a biphasic calcium phosphate ceramic is dependent on the HAp/beta-TCP ratio: the higher the ratio, the lower the extent of dissolution. Biphasic calcium phosphates are osteoconductive but not osteoinductive.

The tissue response to porous HAp differs from that of dense HAp in that porous HAp allows bone ingrowth, i.e., is osteoconductive. Porosity and interconnectivity determine the amount and type of ingrowth. For implants with a high degree of porosity and interconnectivity, tissue ingrowth begins after 3 or 4 days. After 28 days the ingrowth is complete. The bone-HAp bonding found within the pores is similar to that in dense HAp.

One of the most attractive features of calcium phosphates is their ability to become strongly bonded to living bone. The bond is so strong, that implants cannot be detached from the adjoining bone without fracturing either the implant or the bone (Jarcho, M., Biomaterial Aspects of Calcium Phosphates, *Dental Clinics of North America,* 30, 1986, 25-47.).

The most common method used to prepare calcium phosphate bioceramics, such as HAp and TCP, involves the use of powders prepared from aqueous solutions of the starting chemicals. These powders are compacted under high pressure (10 to 20,000 psi) and then sintered at between 1000° C. and 1300° C. See Jarcho, 1986. Biphasic calcium phosphate (BCP) is obtained when calcium-deficient biologic or synthetic apatites are sintered at or above 700° C. An apatite is considered calcium deficient when the Ca/P ratio is less than the stoichiometric value of 1.67 for pure calcium hydroxyapatite. However, sintering at high temperatures causes low porosity, closed pores, and poor phase purity (due to decomposition), while sintering at lower temperatures to increase porosity produces weak bonds (Brown, P., et al., Factors Influencing the Formation of Monolithic Hydroxyapatite at Physiological Temperature, in Rusin, R. P., et al. eds., *Bioceramics. Materials and Applications II* (*Ceramic Transactions* v63), American Ceramic Society, Westerville, Ohio, 1995, pp. 37-48.) Thus sintering is inadequate for producing HAp implant material for structural bone replacement.

Stoichiometric calcium hydroxyapatite ceramics, especially if it is heated at high temperatures, do not take part in the bone remodeling process due to the loss of carbonate ions at high temperatures. The ideal Ca/P ratio of HAp is 10:6 (1.66667), and the calculated density is 3.219 g/cm$^3$. Calcium phosphate can be crystallized into salts, hydroxyapatite, and beta-whitlockite depending on the Ca/P ratio, presence of water, impurities, and temperature. However, in many cases, more than one structure will exist in the same product. At lower temperatures (<900° C.) and wet environments it is more likely that hydroxyapatite will form. At higher temperatures and in dry atmospheres beta-whitlockite will be formed.

Precipitates of hydroxyapatites can be made from an aqueous solution of $Ca(NO_3)_2$ and $NaH_2PO_4$. One method uses precipitates that are filtered and dried to form a fine particle powder. After calcination for 3 hours at 900° C., the powder is pressed into a final form and sintered at about 1050° C. to 1200° C. for 3 hours. Macroporosity can be generated by incorporating volatile materials (naphthalene or hydrogen peroxide), heating at a temperature below 200° C., and then sintering.

A good bioceramic should have an interconnected porosity between 55 and 70 percent, and the pore size should range from 150 to 700 µm as in natural bone. An ideal cancellous bone graft substitute would mimic osteon-evacuated cancellous bone and have a thin lattice interconnected by pores of 500-600 micrometers. Since the Haversian systems are about 190-230 micrometers in diameter, an ideal bone graft material for cortical bone regeneration would have an interconnected porous system of similar dimensions.

Polymer-ceramic composites and polymer meshworks have been developed to provide suitable porosity, generally at the expense of desirable mechanical properties. See Yang, et al., The design of scaffolds for use in tissue engineering. Part I. Traditional factors, *Tissue Eng.* 2001 7(6): 679-689; Pompe, W., et al., Functionally graded materials for biomedical applications, *Materials Science and Engineering* 2003 A362: 40-60.

SUMMARY OF THE INVENTION

In light of the foregoing, it is an object of the present invention to provide one or more calcium phosphate compositions and/or methods for their use and/or preparation, thereby overcoming various deficiencies and shortcomings of the prior art, including those outlined above. It will be understood by those skilled in the art that one or more aspects of this invention can meet certain objectives, while one or more other aspects can meet certain other objectives. Each objective may not apply equally, in all its respects, to every aspect of this invention. As such, the following objects can be viewed in the alternative with respect to any one aspect of this invention.

It is an object of the present invention to provide a resorbable and osteoconductive synthetic bone graft material comprising a calcium phosphate mineral matrix lattice interpenetrated by a substantially interconnected network of pores. As another object, the present invention provides a method of making such a synthetic bone graft material wherein a mineral matrix lattice and a substantially interconnected network of removable inorganic porogen are formed simultaneously by controlled spinodal decomposition of a molten mixture of inorganic starting materials.

Other objects, features, benefits and advantages of the present invention will be apparent from this summary and descriptions of certain embodiments, and will be readily apparent to those skilled in the art having knowledge of various biomimetic bone materials and production techniques. Such objects, features, benefits and advantages will be apparent from the above as taken into conjunction with the accompanying examples, data, figures and all reasonable inferences to be drawn therefrom, alone or with consideration of the references incorporated herein.

In part, the present invention can comprise a calcium phosphate composition comprising a first phase comprising hydroxyapatite and tricalcium phosphate, and a second phase comprising a removable inorganic porogen, with the second phase substantially interconnected continuously within the first phase, with an interconnection of a substantially constant or uniform cross-sectional dimension. In certain embodiments, as discussed elsewhere herein, the removable porogen component can comprise a transition metal oxide, such a component including but not limited to iron oxide, nickel oxide, cobalt oxide, manganese oxide and copper oxide. In various other embodiments, as can be contemplated by those skilled in the art, a porogen component can also comprise a combination of transition metal oxides. For purpose of illustration, without limitation to any one porogen or relative component concentration, such a composition can comprise an iron oxide content ranging from about 25 wt. % to about 65 wt. %, a calcium oxide content ranging from about 25 wt. % to about 45 wt. %, and a phosphorous oxide content ranging from about 10 wt. % to about 30 wt. %.

In various other embodiments, the compositions of this invention can be provided absent an aforementioned porogen component, such a porogen at least partially removed, providing a compositional matrix of substantially, continuously interconnected pores. In such embodiments, the matrix can have a porosity ranging from about 30% to about 60%. Regardless, pore size can range from about 3 µm to about 700 µm. In various other embodiments, the porosity can range from about 55% to about 70%. Again, without limitation to any particular porosity parameter, such a matrix can have a pore size ranging from about 500 µm to about 600 µm, ranging from about 190 µm to about 230 µm, ranging from about 3 µm to about 30 µm, or having a size less than about 1.5 µm in cross-sectional dimension.

Alternatively, this invention can comprise a calcium phosphate spinodal decomposition product of a mixture comprising iron oxide, calcium oxide and calcium phosphate, such a product within the immiscibility region of a phase diagram of a $CaO$—$P_2O_5$—$FeO_n$ ternary system. Such a product can comprise an iron oxide, calcium oxide and phosphorous oxide contents ranging as discussed elsewhere herein. Without limitation, certain product embodiments can comprise an iron oxide content of about 40 wt. %, a calcium oxide content of about 37.5 wt. % and a phosphorous oxide content of about 22.5 wt. %. Regardless of particular component content or weight percent, various products of this invention can comprise a Ca/P ratio between about 1.5 and about 2.0. Likewise, without regard to component content or weight percent, certain embodiments of such products can provide a wavelength of less than about 3 μm.

The present invention can provide porous calcium phosphate compositions that are biocompatible, biodegradable, and osteoconductive useful as synthetic bone material. Accordingly, in certain embodiments, the present invention can provide a method of using a ternary system to prepare a biomimetic bone material. Such a method can comprise (1) providing a mixture of a transition metal oxide, calcium oxide and calcium phosphate components, each component in an amount sufficient to provide a spinodal decomposition product within the immiscibility region of a phase diagram of a $CaO-P_2O_5$-MO ternary system, where MO can be selected from available transition metal oxides; (2) heating the mixture over a temperature range and a time sufficient for spinodal decomposition of a mixture and (3) removing the MO component from the decomposition product, to provide a biomimetic bone material. As discussed more fully below, and as would be understood by those skilled in the art, such heating can comprise raising mixture temperature up to about or beyond mixture melting point, holding any such temperature, and cooling or quenching the mixture to a temperature below any raised, melt and/or hold temperature to effect spinodal decomposition. As illustrated below, such a mixture can be melted, then cooled at a rate sufficient to affect product microstructure. In various other embodiments, the amount of the MO component and/or the rate of cooling can be used to affect or control material porosity upon removal of the MO component, such removal as can be achieved using an acid, a chelating agent or combination thereof. Depending upon material porosity, such a material can have a pore dimension to mimic, for example, cancellous or cortical bone.

In certain other embodiments, the present invention can provide a method of making a porous material, such a method comprising selection of chemical components, including a removable inorganic porogen, in a ratio that provides a desired porosity in the product; mixing the selected chemical components; heating the mixture of the chemical components to melt the mixture; controlling the cooling of the molten mixture to induce spinodal decomposition of the mixture into a material comprising a first phase comprising hydroxyapatite and a second phase comprising an inorganic porogen; and removing the inorganic porogen to provide a porous material having a substantially interconnected network of pores.

In preferred embodiments, the porous hydroxyapatite material produced has an porosity of about 55 to about 70 percent. Regardless of porosity, in certain embodiments the pore size can range from about 3 μm to about 700 μm. In other embodiments, useful as cancellous bone graft substitutes, the material can mimic cancellous bone structure, having a thin lattice comprising hydroxyapatite and beta-tricalcium phosphate interpenetrated by a network of substantially interconnected pores about 500- about 600 μm in diameter. In other embodiments, useful as cortical bone graft substitutes, the material can have a substantially interconnected network of pores about 190- about 230 μm in diameter. In yet other embodiments, the material can comprise hydroxyapatite and beta-tricalcium phosphate interpenetrated by a network of substantially interconnected pores about 3- about 30 μm in diameter. Alternatively, certain compositions of this invention can provide a material exhibiting a microstructural wavelength less than about 3 μm and/or characterized by pores dimensioned less than about 1.5 μm.

In certain embodiments, the present invention provides porous compositions comprising hydroxyapatite and tricalcium phosphate wherein the substantially interconnected pores are formed by spinodal decomposition induced by controlled heating and/or cooling of a molten mixture of calcium oxide, phosphorous pentoxide and a removable inorganic porogen followed by chemical removal of the inorganic porogen from the solidified mixture. Suitable inorganic porogens can be selected from transition metal oxides, including but not limited to iron oxide, nickel oxide, cobalt oxide, manganese oxide and copper oxide. As discussed herein, a useful transition metal oxide is an iron oxide.

Spinodal decomposition involves a thermodynamic separation of a single-phase liquid into an interconnected, two-phase liquid with a continuous network. As mentioned above, the primary phase can comprise a mixture of hydroxyapatite (HAp, $Ca_{10}(PO_4)_6(OH)_2$) and tricalcium phosphate (TCP, $Ca_3(PO_4)_2$). A secondary phase, iron oxide in some embodiments, may be dissolved, leaving a porous, substantially continuously-connected structure of HAp and TCP. The porosity can be modified by varying amounts of the initial compositional components, while the pore size can be changed by varying the time and temperature history. Since TCP resorbs faster than HAp in the body, the resorption rate can be controlled by altering the range of available HAp/TCP ratios through component mixing and/or solution treatment after the second phase is removed. (See, e.g., Malysheva, et al., *Inorganic Materials*, Vol. 37, No. 2, 179-183, 2001.) Control of these process variables allows the implant material to be tailored to a specific application.

The resulting porous materials of the present invention can be used to make bone graft products specifically designed to match the characteristics of specific bone types. Accordingly, the present invention also provides articles of manufacture, such as a sterile porous material comprising a porous material comprising hydroxyapatite in a single-use sterile package, such sterilization and packaging techniques as would be understood by those skilled in the art.

BRIEF DESCRIPTION OF THE DRAWINGS

FIG. 1A shows a photomicrograph of normal cancellous bone of a 30 year old woman and FIG. 1B shows a photomicrograph of osteoporotic cancellous bone from a 60 year old woman, whether the mineral appears as dark areas, and pores appear as light areas.

FIGS. 7A-7J provide a diagrammatic representation of exemplary electron micrographs of sections of samples related to the final composition of the sample represented on the phase diagram (FIG. 7A) of the CaO—$P_2O_5$—FeO ternary system of FIG. 4.

DETAILED DESCRIPTION OF THE INVENTION

Certain porous hydroxyapatite materials of the present invention are formed using controlled spinodal decomposition. Spinodal decomposition involves a thermodynamic separation of a single-phase liquid into two interconnected, liquid phases having continuous networks. In some embodiments, the ternary CaO—$P_2O_5$—FeO system is used. The resulting primary phase will be a mixture of hydroxyapatite (HAp, $Ca_{10}(PO_4)_6(OH)_2$) and tricalcium phosphate (TCP, $Ca_3(PO_4)_2$), both of which are calcium phosphates. The secondary phases comprises a removable inorganic porogen, preferably iron oxide, which can be preferentially dissolved and/or removed, leaving a porous, substantially continuously connected structure of HAp and TCP.

The porosity can be modified by varying the initial composition, specifically by selecting the ratio of inorganic porogen to the other starting components. The pore size can be changed by controlling the time-temperature history, in particular the rate of cooling of the molten mixture of starting components. In addition, since TCP resorbs faster than HAp in the body, the resorption rate of the bone graft material can be controlled by altering the HAp/TCP ratio through solution treatment after the second phase is removed. Control of these process variables allows the implant material to be tailored to the specific application. Different bones and regions of bones have different porosities and pore sizes; therefore, control of these characteristics is highly desirable.

Bioactive and resorbable ceramics are useful for the fabrication of implants which densely fuse with bone (for example, in skull restorations after operations or trauma), tooth root implants, biological tooth fillings, cure of diseases of the periodontia (tissue around teeth), maxillofacial reconstruction, grafting and stabilizing skull bone, joint reconstruction, endoprosthesis of hearing aids, cosmetic eye prostheses, etc. Resorbable ceramics are also used in the restoration of tendons, ligaments, small blood vessels, and nerve fibers. Forming the bone graft material using spinodal decomposition can lower the cost of producing the material, lower than that for currently available materials, making synthetic bone replacement available to patients who otherwise could not afford it.

Figure 1:
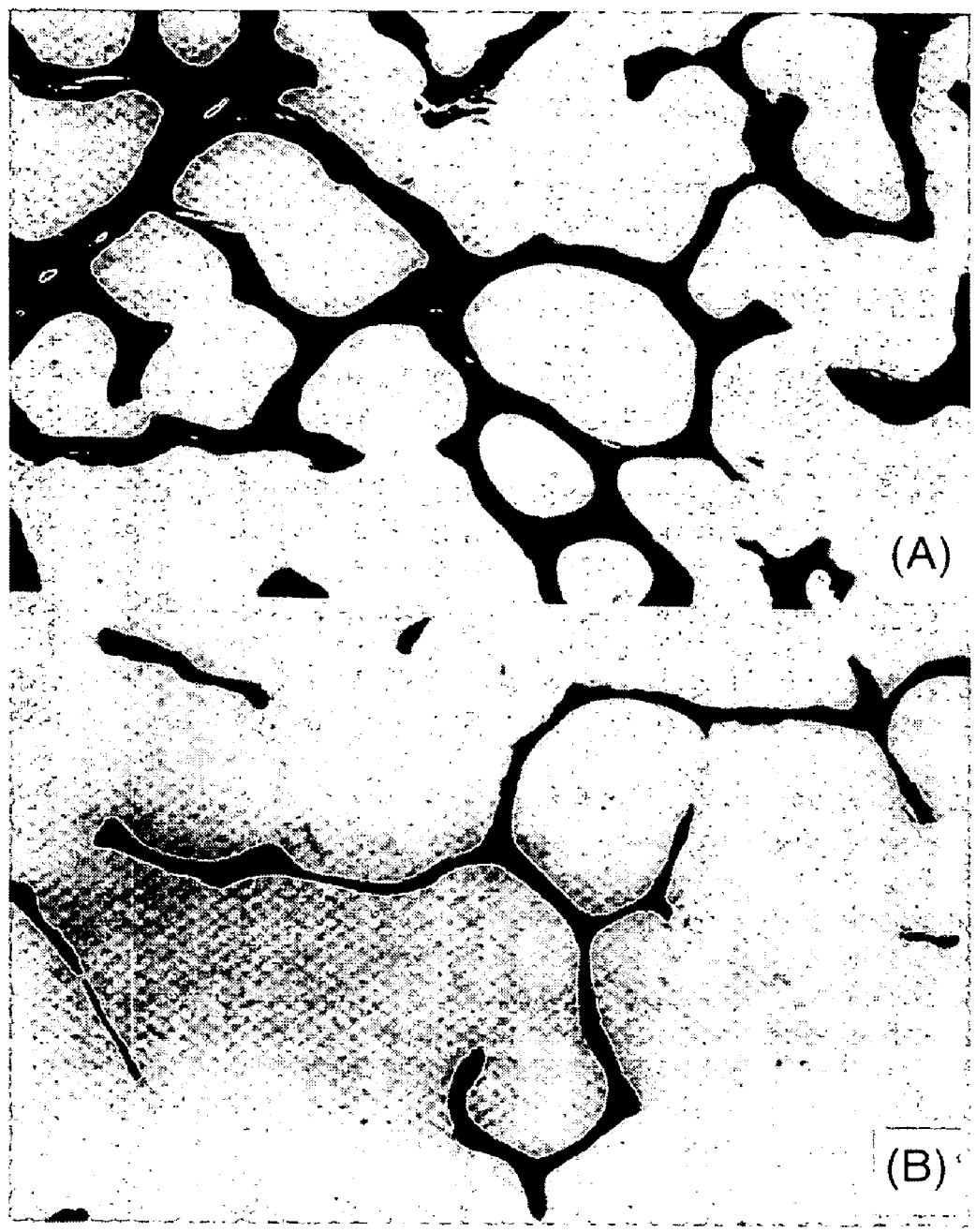
FIGS. 1A and 1B show a comparison of photomicrographs between normal bone and osteoporotic bone.
Figure 2:
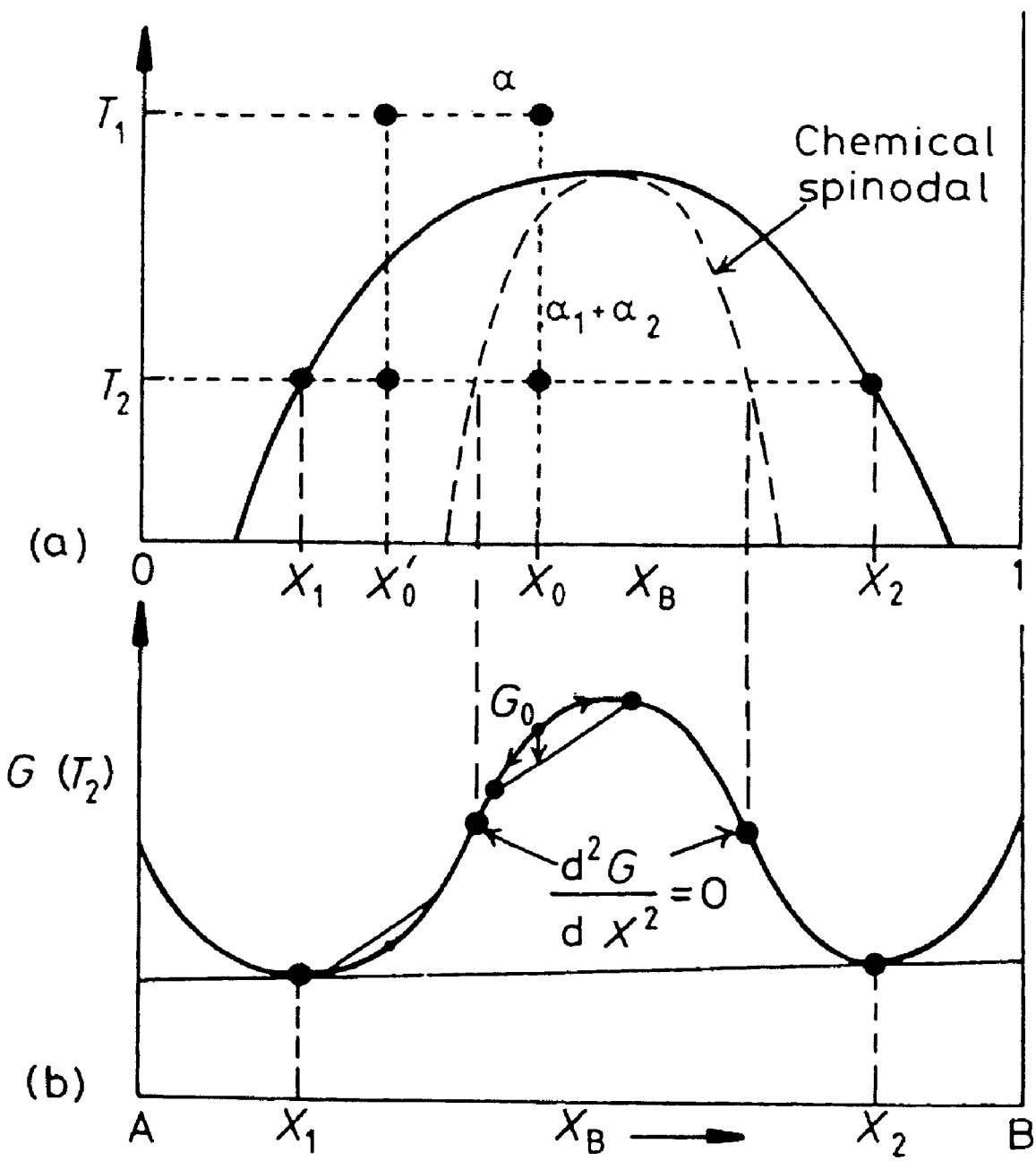
FIGS. 2A and 2B are diagrams showing in FIG. 2A an exemplary phase diagram showing chemical spinodal and in FIG. 2B, an exemplary free energy diagram (Porter, D., & Easterling, K., *Phase Transformations in Metal and Alloys*, 2$^{nd}$ Ed., Nelson Thornes, Cheltenham, UK, 2001).

Liquids are not always completely soluble in one another, but may exhibit liquid immiscibility which causes the liquids to separate into two phases. The phase diagram of such a ternary system contains an immiscibility region, and thus undergoes spinodal decomposition without the addition of another material. This characteristic allows use of this ternary system to control of the pore size, porosity, and chemistry. FIG. 2 illustrates diagrammatically characteristics of a sample system of a mixture of A and B. FIGS. 2A and 2B are diagrams showing in FIG. 2A an exemplary phase diagram showing chemical spinodal and in FIG. 2B, an exemplary free energy diagram (Porter, D., & Easterling, K., *Phase Transformations in Metal and Alloys*, $2^{nd}$ Ed., Nelson Thornes, Cheltenham, UK, 2001). If an alloy of composition $X_0$ is heated to temperature $T_1$ and then quenched to $T_2$, its composition will initially be homogeneous and its free energy will be $G_0$ as shown in part (b) of the figure. However, the alloy can decrease its free energy by separating into A-rich regions and B-rich regions. Therefore, the alloy will phase separate until compositions $X_1$ and $X_2$ are reached. In the case of spinodal decomposition, both phases are continuous with diffuse boundaries. Spinodal decomposition occurs when $d^2G/dX^2<0$.

Figure 3:
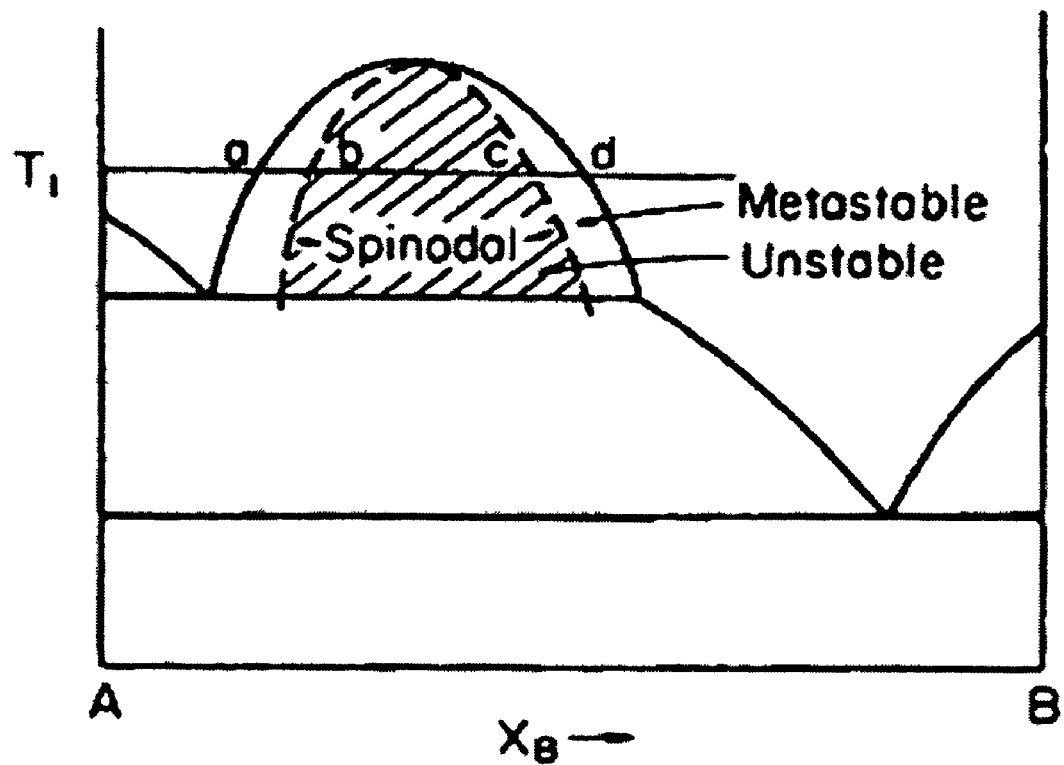
FIG. 3 is a diagram illustrating differences between meta-stable and unstable phase separation (Bergeron, C. G., & Risbud, S. H., *Introduction to Phase Equilibrium in Ceramics*, American Ceramic Society, Columbus, Ohio, 1984).

FIG. 3 shows a binary phase diagram with a liquid miscibility gap, illustrating differences between metastable and unstable phase separation (Bergeron, C. G., & Risbud, S. H., *Introduction to Phase Equilibrium in Ceramics,* American Ceramic Society, Columbus, Ohio, 1984).

A melt between a and b or c and d is metastable and will remain a homogeneous liquid unless the secondary phase is nucleated. In order to nucleate the second phase, some discontinuity, such as a container wall, a bubble, or an impurity, must be present for a stable nucleus to form. A melt with composition between b and c is unstable and will separate into two liquid phases as discussed above. When an initially homogeneous single phase is cooled through the unstable region, two completely interpenetrating phases are formed, each with a high degree of connectivity. Differences between metastable and unstable phase separation are summarized in Table 2, below.

TABLE 2

Differences between metastable and unstable phase separation

| Nucleation and Growth | Spinodal Decomposition |
| --- | --- |
| Invariance of second phase composition to time at constant temperature | Continuous variation of both extremes in composition with time until equilibrium compositions are reached |
| Interface between phases is always same degree of sharpness during growth | Interface between phases initially is very diffuse, eventually sharpens |
| Tendency for random distributions of particle sizes and positions in matrix | Regularity of second phase distribution in size and position characterized by a geometric spacing |
| Tendency for separation of second phase spherical particles with low connectivity | Tendency for separation of second phase, non-spherical particles with high connectivity |

Figure 4:
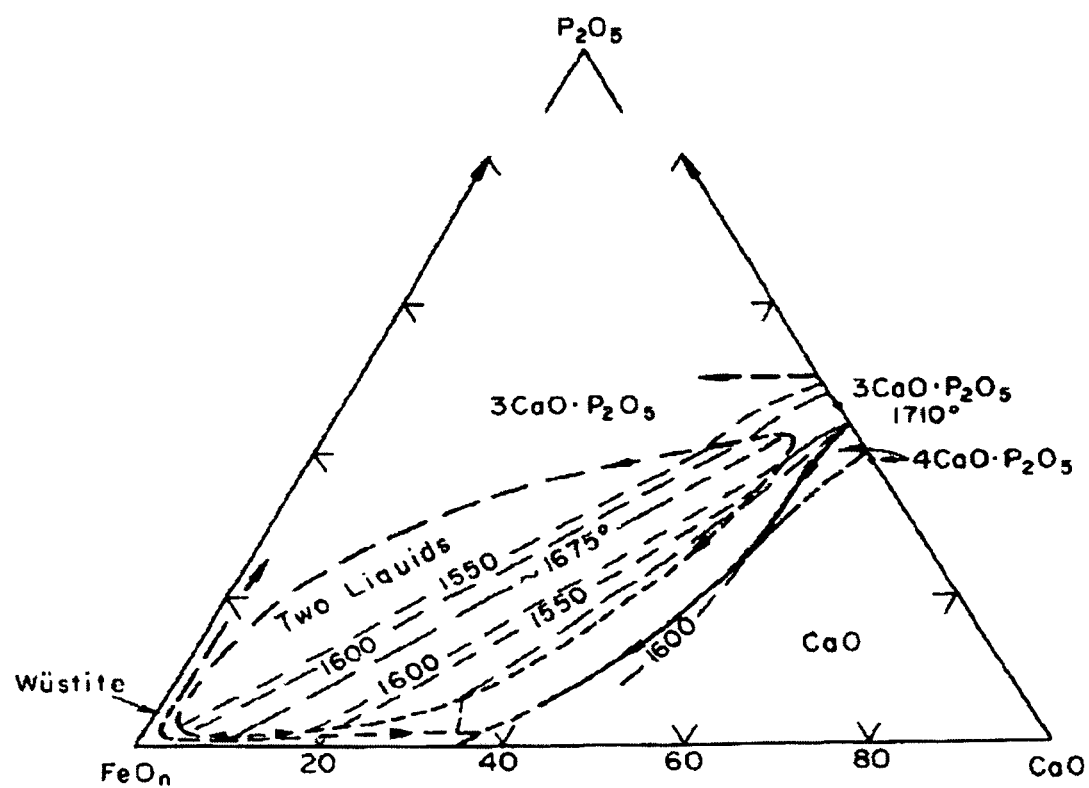
FIG. 4 is a phase diagram of the $CaO-P_2O_5$-FeO ternary system showing the miscibility region bounded by dashed lines (Levin, E., et al., *Phase Diagrams for Ceramists*, American Ceramic Society, Westerville, Ohio, 1984).

The phase diagram of a preferred ternary system is shown FIG. 4. FIG. 4 is a phase diagram of the $CaO$—$P_2O_5$—$FeO$ ternary system showing the miscibility region bounded by dashed lines (Levin, E., et al., *Phase Diagrams for Ceramists,* American Ceramic Society, Westerville, Ohio, 1984).

To prepare compositional samples, mixture of starting materials is generated, using the phase diagram served as a guide for choosing the compositions to be analyzed. At first, compositions towards the middle of the immiscibility region were tested.

Figure 5:
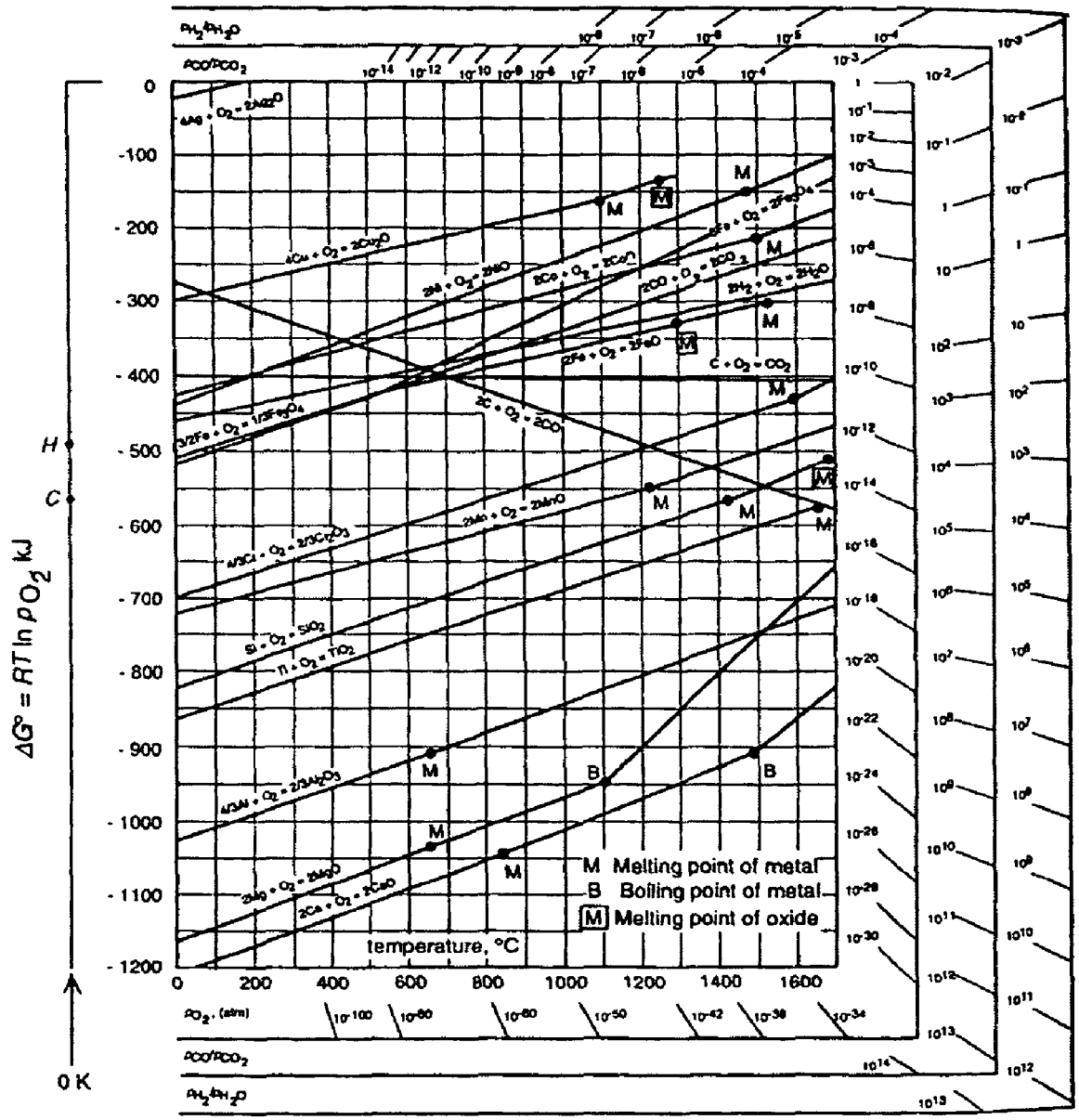
FIG. 5 is an Ellingham diagram (Gaskell, D. R., *Introduction to the Thermodynamics of Materials*, 3rd Ed., Taylor & Francis, Philadelphia, 1995).

In certain embodiments, samples were made from the starting components of iron oxide ($Fe_2O_3$), calcium oxide (CaO), and calcium phosphate ($Ca_2P_2O_7$). The ratios of the starting materials were calculated from the desired final compositions in the phase diagram (FIG. 4), with a supplementary amount of CaO. By consulting the Ellingham diagram, which is shown in FIG. 5, it was determined that $Fe_3O_4$ would be the stable polymorph of iron oxide at the temperatures used (Gaskell, D. R., *Introduction to the Thermodynamics of Materials,* 3rd Ed., Taylor & Francis, Philadelphia, 1995).

In this system, calcium phosphate decomposes to calcium oxide with a stoichiometry similar to the following:

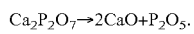

The iron oxide transforms as shown:

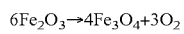

Figure 6:
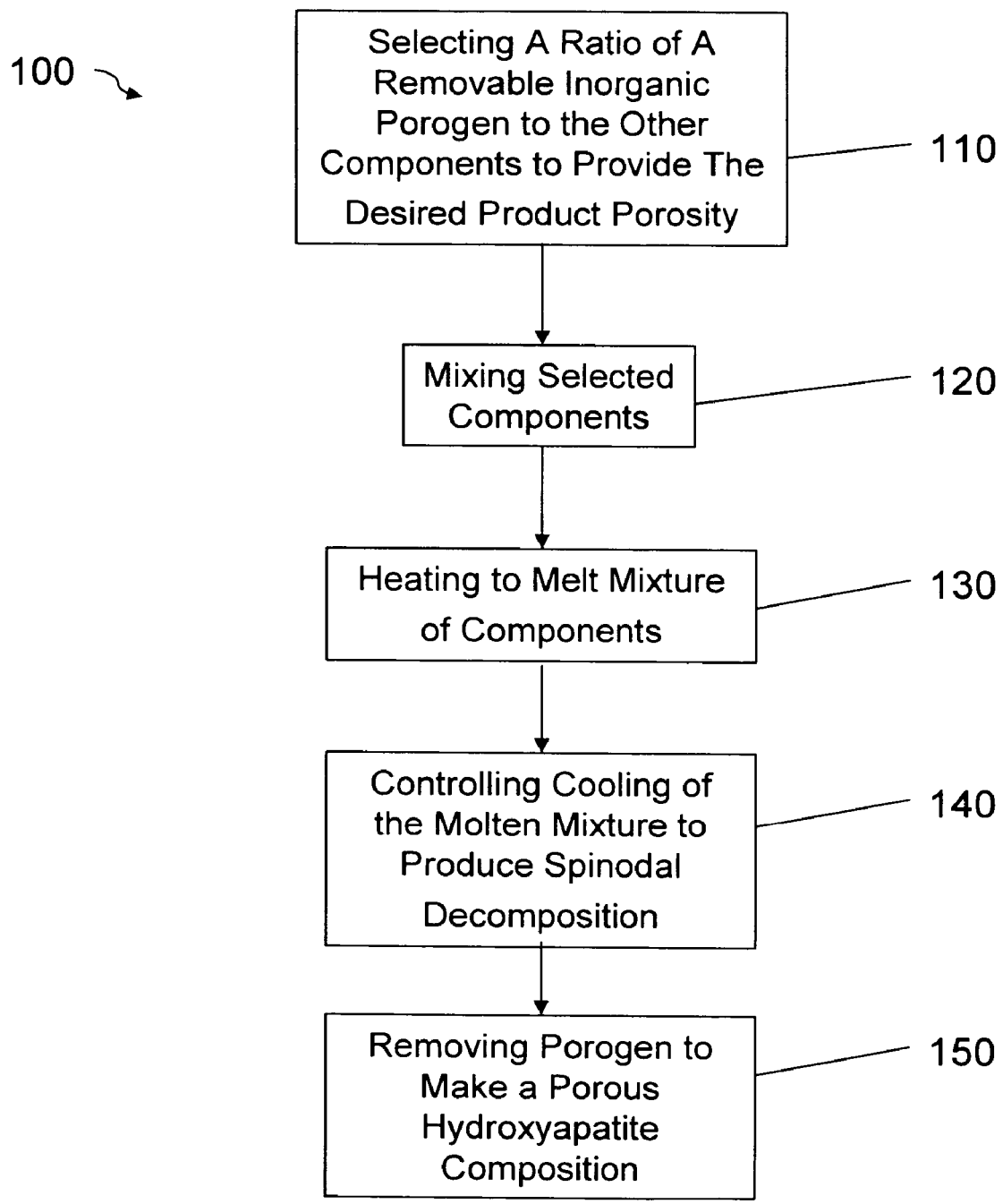
FIG. 6 is a diagrammatic representation illustrating a method 100 of making a porous hydroxyapatite composition showing steps of selecting 110 the ratio of chemical components to provide a desired porosity in the product, mixing 120 the selected chemical components, heating 130 the mixture of the chemical components, controlling 140 the cooling of the mixture to produce spinodal decomposition into a first phase and a second phase, and removing 150 the second phase to make a porous hydroxyapatite composition.

FIG. 6 is a diagrammatic representation illustrating a method 100 of making a porous hydroxyapatite composition: content concentration and/or selecting 110 the ratio of chemical components to provide a desired porosity in the product, mixing 120 the selected chemical components, heating 130 the mixture of the chemical components, controlling 140 the cooling of the mixture to produce spinodal decomposition into a first phase and a second phase, and removing 150 the second phase to provide a porous hydroxyapatite composition. Selecting 110 is done with reference to the phase diagram, such as shown in FIG. 4, of a ternary system of calcium oxide, phosphate and a transition metal oxide. A preferred transition metal oxide can be iron oxide. The transition metal oxide serves as an inorganic porogen that is removed in step 150, below.

Table 3, below, provides the starting percentages of components and the final chemical composition for seven non-limiting embodiments ranked in order of final $Fe_3O_4$ composition. In this series of embodiments, $Fe_3O_4$ was used as the transition metal oxide porogen; the relative amount of $Fe_3O_4$ can determine the relative ranking of porosity in the final product. Good results have been obtained with 210G, with a final composition of 37.5% CaO, 40.0% $Fe_3O_4$, 22.5% $P_2O_5$ (weight percent). Samples made with this and similar chemical compositions have shown spinodal decomposition.

TABLE 3

Exemplary Compositions

| | Starting Components (wt %) | | | Final Composition (wt %) | | | |
| --- | --- | --- | --- | --- | --- | --- | --- |
| KEY | $Fe_2O_3$ | CaO | $Ca_2P_2O_7$ | $Fe_3O_4$ | CaO | $P_2O_5$ | Figure |
| 200B | 30.6 | 51.1 | 18.3 | 30 | 43 | 27 | 7B |
| 202C | 40.8 | 10.6 | 48.6 | 40 | 32.5 | 27.5 | 7C |
| 210G | 38.5 | 37.5 | 24.0 | 40 | 37.5 | 22.5 | 7G, 7H, 8, 10, 11, 13, 14 |
| 212I | 40.8 | 23.9 | 35.3 | 40 | 40 | 20 | 7I, 7J |
| 204D | 45.8 | 18.9 | 35.3 | 45 | 35 | 20 | 7D |
| 206E | 50.8 | 39.6 | 9.6 | 50.0 | 27.5 | 22.5 | 7E, 12 |
| 208F | 60.8 | 20.0 | 19.2 | 60 | 29 | 11 | 7F |

Samples of ten grams were made by using the weight percentages from the phase diagram. For example, if a sample consisting of 40.0% $Fe_3O_4$-37.5% CaO-22.5% $P_2O_5$ was desired, the sample would be made to form 4.0 g $Fe_3O_4$, 3.75 g CaO, and 2.25 g $P_2O_5$.

In order to calculate the correct amount of starting powders, the previously shown chemical equations were converted from molar to mass balanced as follows:

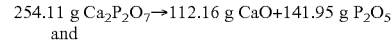

and

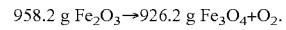

When seeking the previously stated composition, the mass balanced equations would be the following:

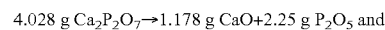

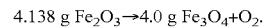

However, this still does not give the required amount of CaO. Therefore, 2.572 g would be added. Any excess oxygen would be released into the environment. The starting powders were mixed well in a porcelain crucible, and then transferred to a platinum crucible for melting.

The step of heating 130 the mixture of the chemical components was performed in a temperature-controlled furnace.

In preferred embodiments, the platinum crucible was placed into a Deltech DT31 vertical tube furnace (Deltech Inc., Denver, Colo.), which was modified by closing ventilation holes in the cabinet. The temperature controller was set for the target temperature, typically about 25-50 degrees Celsius above the melting temperature. The melting temperature was about 1500-1675 degrees Celsius, depending on the particular formulation of starting materials. Once the furnace had reached to the desired temperature, the sample was typically maintained at that temperature for about a half hour.

In certain embodiments, controlling 140 the cooling of the mixture to produce spinodal decomposition was accomplished by rapid quench of the molten mixture by contact with a heat sink, preferably a steel plate. It will be appreciated by the skilled artisan that the rate of cooling of the sample can be influenced by, and thus controlled by, factors such as the temperature differential between the sample and the quench plate, the relative mass of the sample compared to the quench plate and the material of the quench plate, which would determine heat capacity and ability to conduct heat away from the sample in contact with the plate, or by using a material other that steel for the quench plate. Conversely, the rate of cooling of a given size sample can be increased by increasing the temperature differential between the sample and the quench plate by cooling the quench plate, increasing the capacity of the quench plate as a heat sink by increasing the mass of the quench plate. The material used to construct the quench plate must be able to withstand repeated contact with an object of the mass and temperature of the molten sample.

In preferred embodiments, the furnace was quickly unplugged after being maintained near the melting temperature for about one half hour and the molten sample was poured onto a steel plate. The sample was allowed to cool to room temperature before further processing. Occasionally not all of the material would pour from the crucible and a ridge of material would remain on the inside edge of the crucible. This ridge material was retained and examined along with the material that had cooled on the plate.

The sample materials were sectioned using a Buehler ISOMET® Low Speed Saw. The sectioned samples were then mounted in Struers Epofix epoxy and allowed to harden overnight. The mounted samples were polished using standard ceramographic techniques. No etching was necessary to see the microstructure on either an optical microscope or a scanning electron microscope.

The microstructure was typically viewed first using an Olympus Vanox-T optical microscope and photographed with a Kodak Digital Science DC40 camera. Samples were also examined with a FEI Quanta 200 Environmental Scanning Electron Microscope (ESEM). The environmental scanning electron microscope allows the examination and analysis of a specimen whether the specimen is wet or dry, insulating or conducting. It allows a gaseous environment in the specimen chamber, and water reservoir is connected to the specimen chamber for wet analysis. The ESEM has three modes of operation: High Vacuum, Low Vacuum, and ESEM mode. High Vacuum mode is similar to that of traditional SEM. Low Vacuum mode runs at a pressure higher than that of High Vacuum mode but still under vacuum, and ESEM mode allows wet analysis through control of water vapor pressure in the specimen chamber.

Exemplary electron micrographs are shown in FIGS. 7-14. In general, some regions of samples showed nucleation and growth phase separation. Other samples exhibited initial and later stages of spinodal phase separation.

FIGS. 7B-7J provide a diagrammatic representation of exemplary electron micrographs of sections of samples related to the final composition of the sample represented on the phase diagram (FIG. 7A) of the $CaO$—$P_2O_5$—$FeO$ ternary system of FIG. 4. Table 3, above provides the starting mixture and the final composition for seven compositions, with an identifying key linking the entry in Table 3 to the corresponding portion of FIG. 7, e.g. "200B."

Figure 8:
FIG. 8 is a 20× magnification electron micrograph of a section of a sample showing macrosegregation of phases, where pale gray areas represent iron oxide, dark gray areas represent calcium phosphate, black areas represent voids and the scale bar indicates a distance of 2.0 mm.

FIG. 8 is a 20× magnification electron micrograph of a section of a sample showing macrosegregation of phases, where pale gray areas represents iron oxide, dark gray areas represent calcium phosphate, black areas represent voids and the scale bar indicates a distance of 2.0 mm.

Figure 9:
FIG. 9 is a 20× magnification electron micrograph of a section of a sample cooled slowly in the furnace showing a layer of calcium phosphate floating on a layer of iron oxide where, from top to bottom in the figure, the white area represents the crucible in section view, pale gray areas represent iron oxide, dark gray areas represent calcium phosphate, black areas represent voids and the scale bar indicates a distance of 2.0 mm.

FIG. 9 is a 20× magnification electron micrograph of a section of a sample cooled slowly in the furnace ("furnace quench") showing a layer of calcium phosphate floating on a layer of iron oxide where, from top to bottom in the figure, the white area represents the crucible in section view, pale gray areas represent iron oxide, dark gray areas represent calcium phosphate, black areas represent voids and the scale bar indicates a distance of 2.0 mm.

Figure 10:
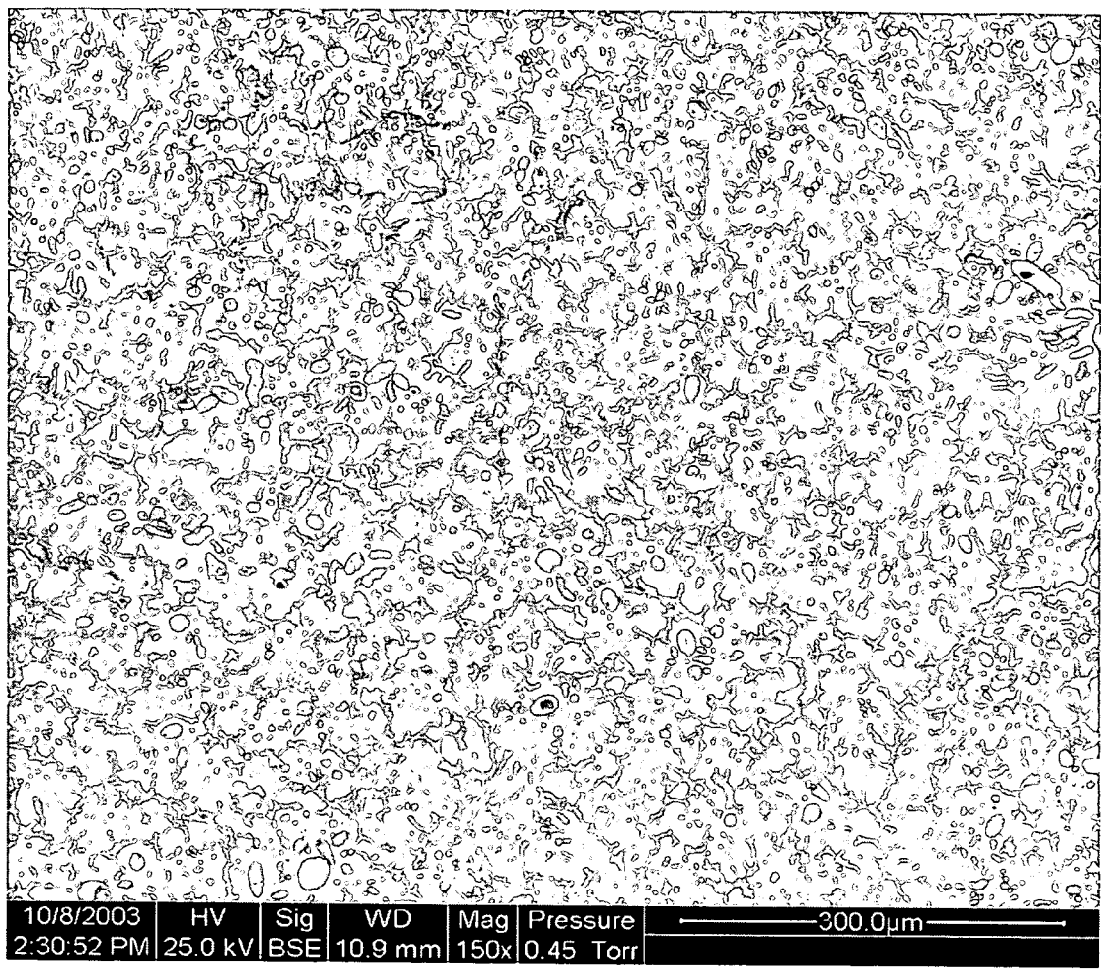
FIG. 10 is a 150× magnification electron micrograph of a section of a sample cooled rapidly by quenching on a steel plate showing a microstructure of interdigitated phases of iron oxide and calcium phosphate separated by spinodal decomposition, where pale gray areas represent iron oxide, dark gray areas represent calcium phosphate, black areas represent voids and the scale bar indicates a distance of 300 µm.

FIG. 10 is a 150× magnification electron micrograph of a section of a sample cooled rapidly by quenching on a steel plate showing a microstructure of interdigitated phases of iron oxide and calcium phosphate separated by spinodal decomposition, where pale gray areas represent iron oxide, dark gray areas represent calcium phosphate, black areas represent voids and the scale bar indicates a distance of 300 µm.

Figure 11:
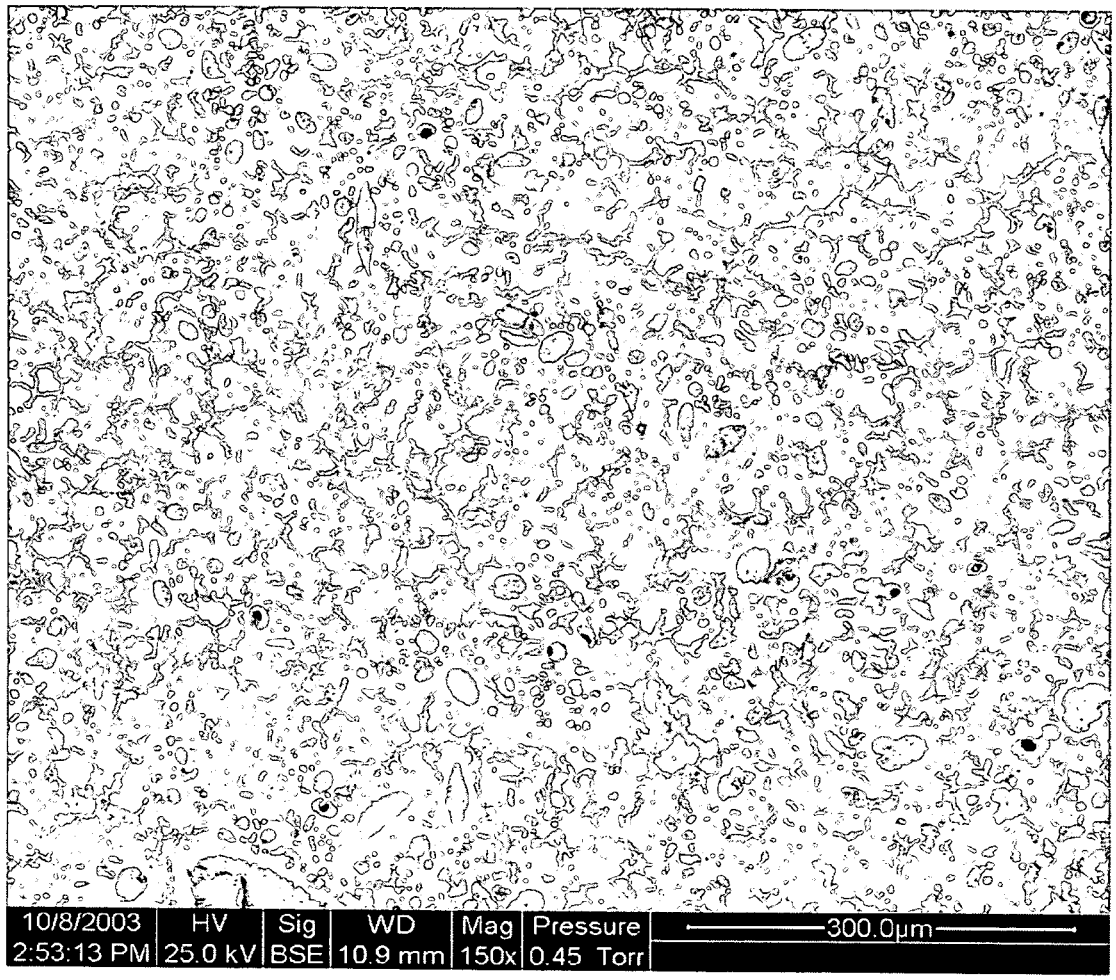
FIG. 11 is a 150× magnification electron micrograph of a section of a sample cooled rapidly by quenching on a steel plate, followed by heat treatment, showing a microstructure similar to that seen in samples not heated treated (FIG. 10), where pale gray areas represent iron oxide, dark gray areas represent calcium phosphate, black areas represent voids and the scale bar indicates a distance of 300 µm.

FIG. 11 is a 150× magnification electron micrograph of a section of a sample cooled rapidly by quenching on a steel plate, followed by heat treatment, showing a microstructure similar to that seen in samples not heated treated (FIG. 10), where pale gray areas represent iron oxide, dark gray areas represent calcium phosphate, black areas represent voids and the scale bar indicates a distance of 300 µm.

The heat treatment was applied to both slowly cooled, i.e. "furnace quenched" and rapidly cooled samples quenched on the heat sink. The sample was heated to a temperature of 1000-1400 degrees Celsius for approximately one half hour and then furnace quenched as described above. Suitable temperatures were about 1025 or about 1200 or about 1400 degrees Celsius. This regime of heat treatment produced a microstructure very similar to samples that were not heat treated. However, a two step heat treatment, first heating the sample above the melting temperature, followed by holding the sample for about twenty minutes at a heat treatment temperature below the melting temperature, followed by furnace quenching did produce a detectable difference in microstructure.

Figure 12:
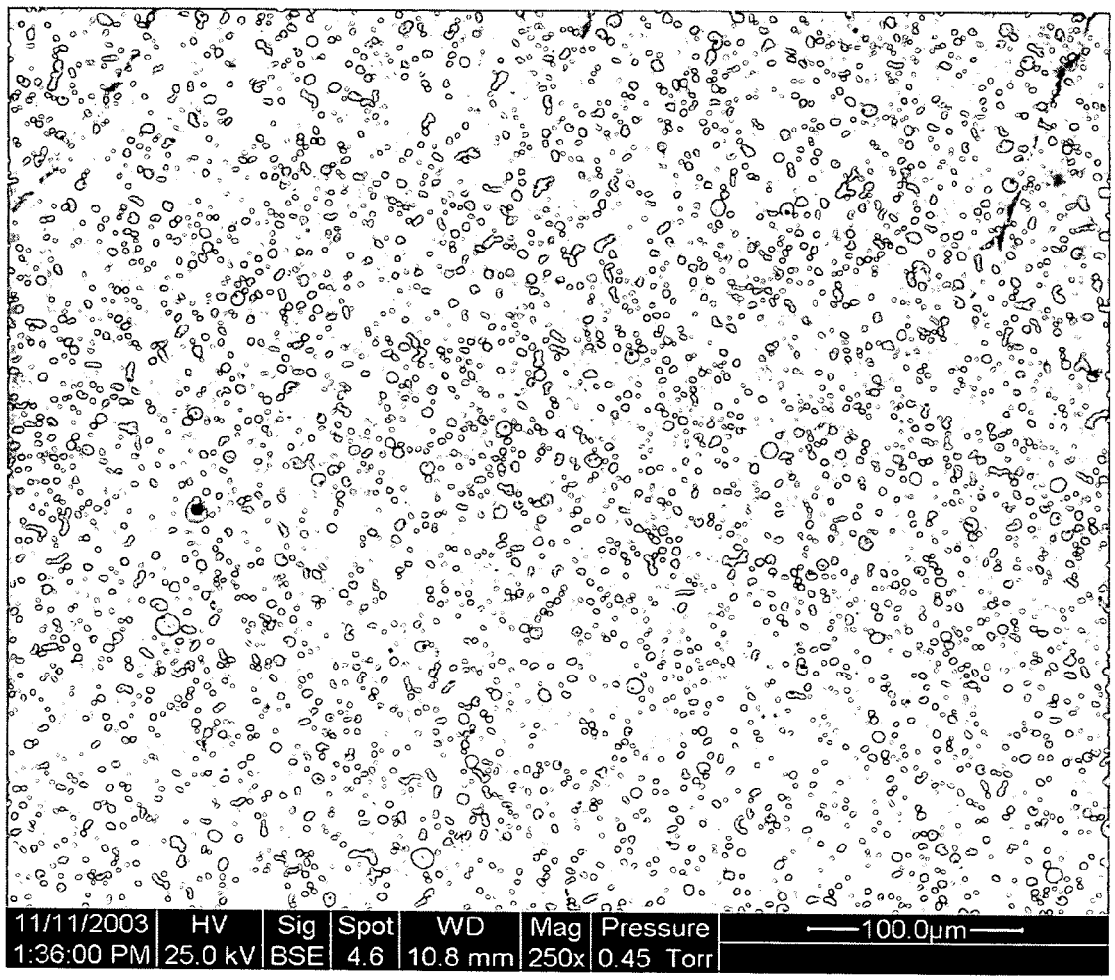
FIG. 12 is a 250× magnification electron micrograph of a section of a sample cooled rapidly by quenching on a steel plate, having a final composition near the boundary of the immiscibility region of the phase ternary system phase diagram (compare to FIG. 7E) showing nucleation and growth phase separation, where pale gray areas represent iron oxide, dark gray areas represent calcium phosphate, black areas represent voids and the scale bar indicates a distance of 100 µm.

FIG. 12 is a 250× magnification electron micrograph of a section of a sample cooled rapidly by quenching on a steel plate, having a final composition near the boundary of the immiscibility region of the phase ternary system phase diagram (compare to FIG. 7E) showing nucleation and growth phase separation, where pale gray areas represent iron oxide, dark gray areas represent calcium phosphate, black areas represent voids and the scale bar indicates a distance of 100 µm.

Figure 13:
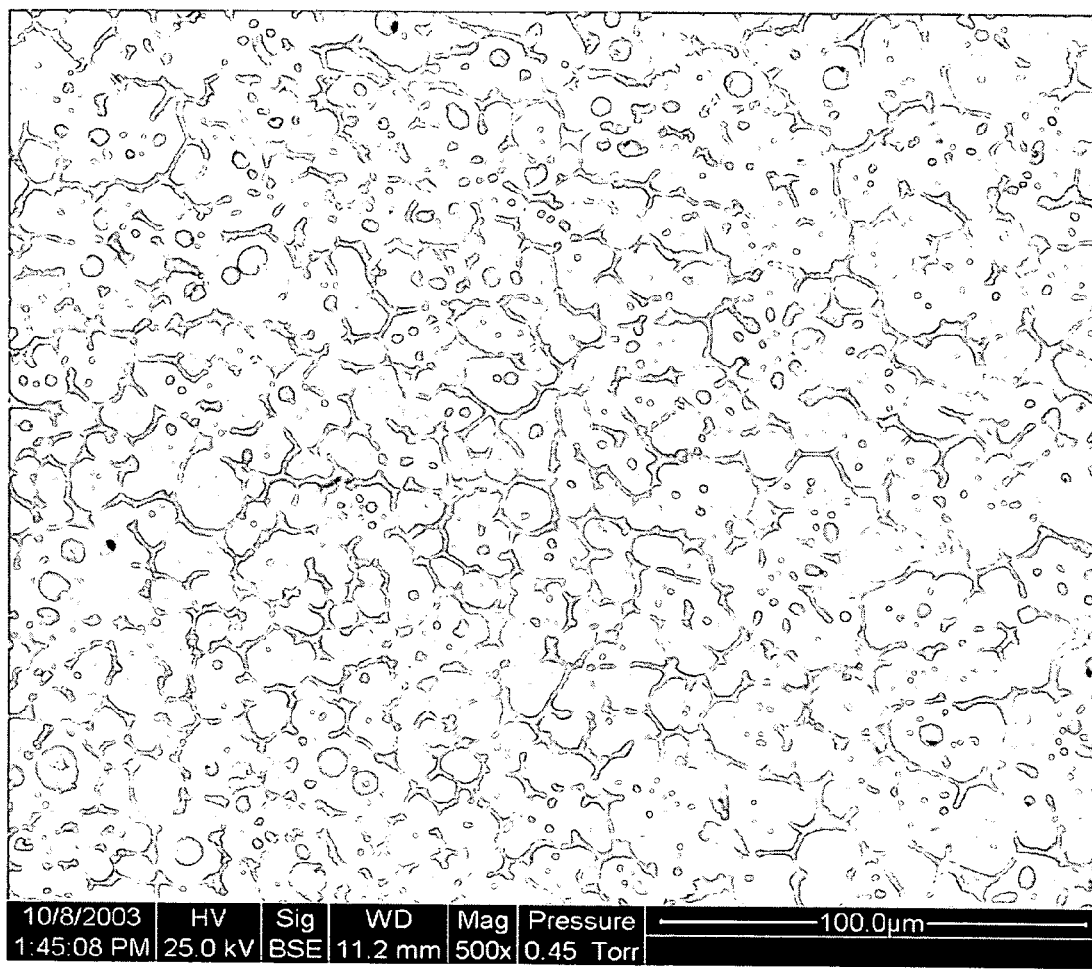
FIG. 13 is a 500× magnification electron micrograph of a section of a sample cooled rapidly by quenching on a steel plate, showing clear separation of phases produced by spinodal decomposition, where pale gray areas represent iron oxide, dark gray areas represent calcium phosphate, black areas represent voids and the scale bar indicates a distance of 100 µm.

FIG. 13 is a 500× magnification electron micrograph of a section of a sample cooled rapidly by quenching on a steel plate, showing clear separation of phases produced by spinodal decomposition, where pale gray areas represent iron oxide, dark gray areas represent calcium phosphate, black areas represent voids and the scale bar indicates a distance of 100 µm.

Figure 14:
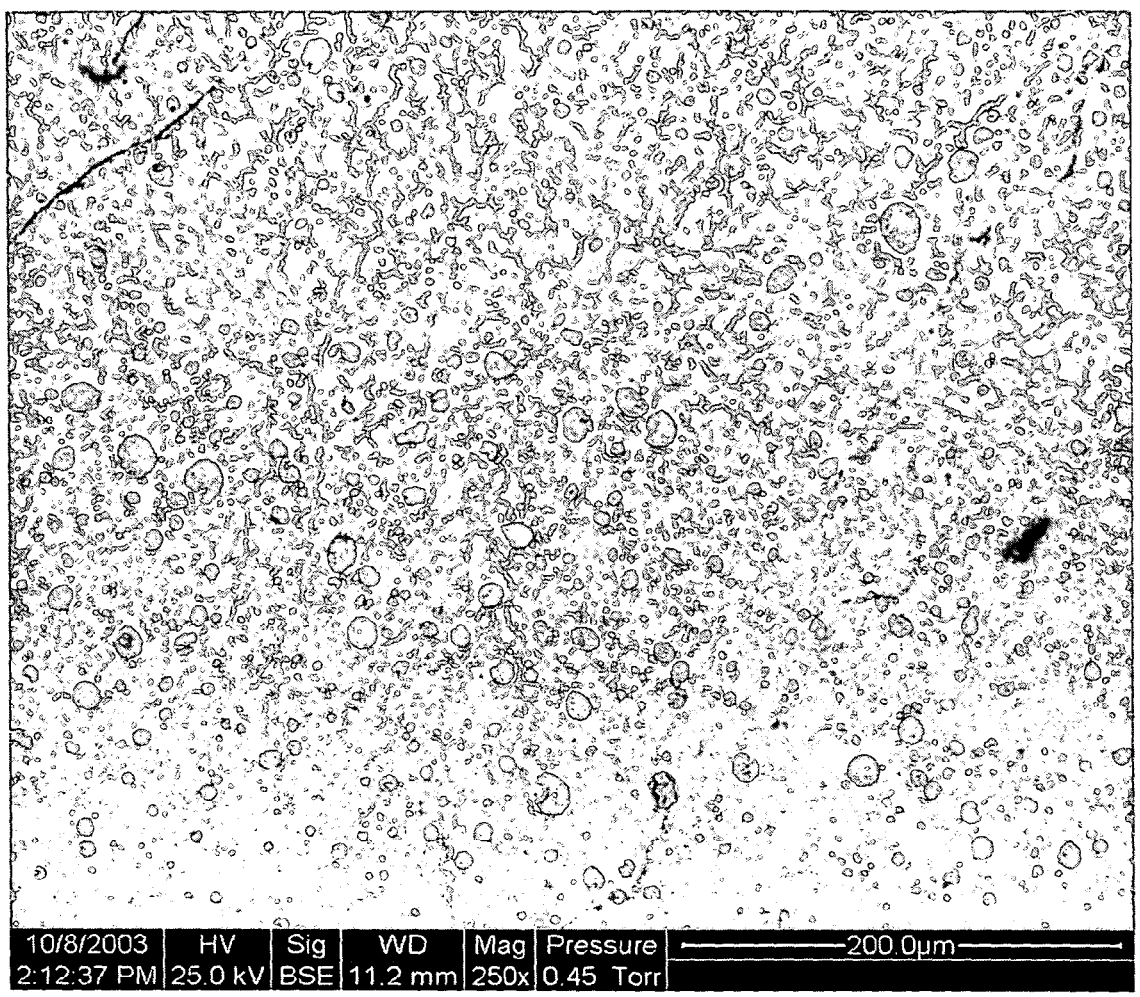
FIG. 14 is a 250× magnification electron micrograph of a section of a sample cooled rapidly by quenching on a steel plate and subsequently heat treated, showing a gradient of the scale or wavelength of the separation of phases produced by spinodal decomposition due to local differences in cooling rate near the quench plate, from the bottom of the electron micrograph where more rapid cooling produces a smaller wavelength microstructure and the top of the electron micrograph where a slower cooling produces a relatively larger wavelength microstructure, and pale gray areas represent iron oxide, dark gray areas represent calcium phosphate, black areas represent voids and the scale bar indicates a distance of 100 µm.

FIG. 14 is a 250× magnification electron micrograph of a section of a sample cooled rapidly by quenching on a steel plate and subsequently heat treated, showing a gradient of the scale or wavelength of the separation of phases produced by spinodal decomposition due to local differences in cooling rate near the quench plate, from the bottom of the electron micrograph where more rapid cooling produces a smaller wavelength microstructure and the top of the electron micrograph where a slower cooling produces a relatively larger wavelength microstructure, and pale gray areas represent iron oxide, dark gray areas represent calcium phosphate, black areas represent voids and the scale bar indicates a distance of 100 μm.

It was clear after examining the products that controlling the duration and rate of cooling of the melted mixture determined both whether spinodal decomposition occurred and the scale, or wavelength, of the microstructure produced by spinodal decomposition. Two regimes of cooling were used: allowing the melted mixture to cool slowly inside the furnace after it was shut off (furnace quench), and rapid cooling by pouring the melted mixture onto a quench plate that served as a high capacity heat sink. Cooled samples could show macrosegregation as shown in FIG. 8, believed to be caused by gross mixing of separate iron oxide and calcium phosphate phases when the melt was poured from the crucible. Samples cooled by furnace quenching showed a macrosegregation in which the calcium phosphate floats on top of the iron oxide, as shown in FIG. 9. The phosphate floating may also explain why ledges form in some samples as shown in FIGS. 7G and 7H and in FIGS. 7I and 7J. The phosphate layer on top of the crucible would cool quickly, especially where it contacts the inside surface of the crucible.

A series of melt-hold-quench tests were performed with a sample of composition 210G (reference, Table 3), a composition of this invention consistently providing spinodal decomposition microstructures. Table 4 summarizes the change in wavelength observed with change in hold temperature. As shown, compositional microstructure and/or porosity can be controlled through the course of thermal treatment.

TABLE 4

Effect of hold temperature on wavelength for the previous microstructures.

| Temperature | Average Wavelength |
| --- | --- |
| Furnace Quench | 0.042 |
| 1625° C. | 0.042 |
| 1550° C. | 0.092 |
| 1500° C. | 0.096 |
| 1450° C. | 0.071 |
| 1425° C. | 0.060 |
| 1400° C. | 0.080 |

Figure 16:
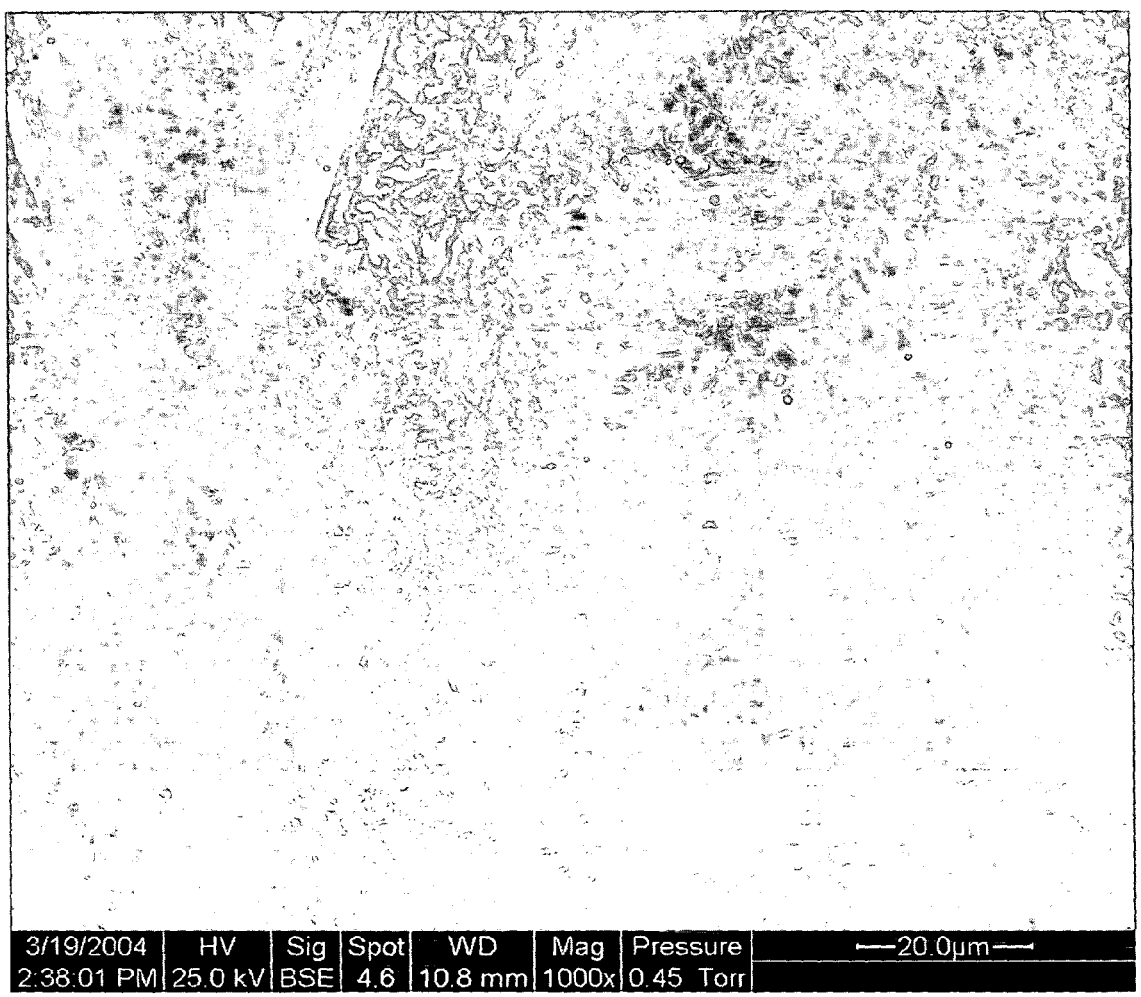
FIG. 16 is a micrograph of a sample transition zone, showing very fine wavelength microstructures.

Further observations were made using a composition with a reduced iron oxide content (28% at $Fe_3O_4$-47.5% CaO-24.5% $P_2O_5$) a composition within the immiscibility dome on the calcium oxide side of the phase diagram. FIG. 16 is a micrograph of the transition zone between the inside and outside zones of the bottom portion of the prepared sample (the outside of the bottom half was positioned closest to the quench plate). As seen in FIG. 16, the wavelength is very fine, less than about 3 μm, corresponding to a pore cross-sectional diameter of less than about 1.5 μm. Without limitation to any one theory or mode of operation, such an observation is believed due to temperature gradients during cooling/quenching. Generally, smallest wavelength microstructures are formed toward the bottom of a compositional sample, which can be attributed to a faster rate of cooling due to quench plate proximity. Larger wavelength microstructures can be observed, in the same sample, in regions of a slower cooling rate. Such wavelength variation further demonstrates microstructural and/or porosity control through choice and course of thermal treatment.

X-ray diffraction analysis was performed on several samples to determine phase presence. For example, the spinodal decomposed region of a sample was crushed into a powder using a porcelain mortar and pestle. The powder was then fixed to a piece of clay forced through the hole of a sample holder, to position the sample flush with the face of the sample holder.

Figure 17:
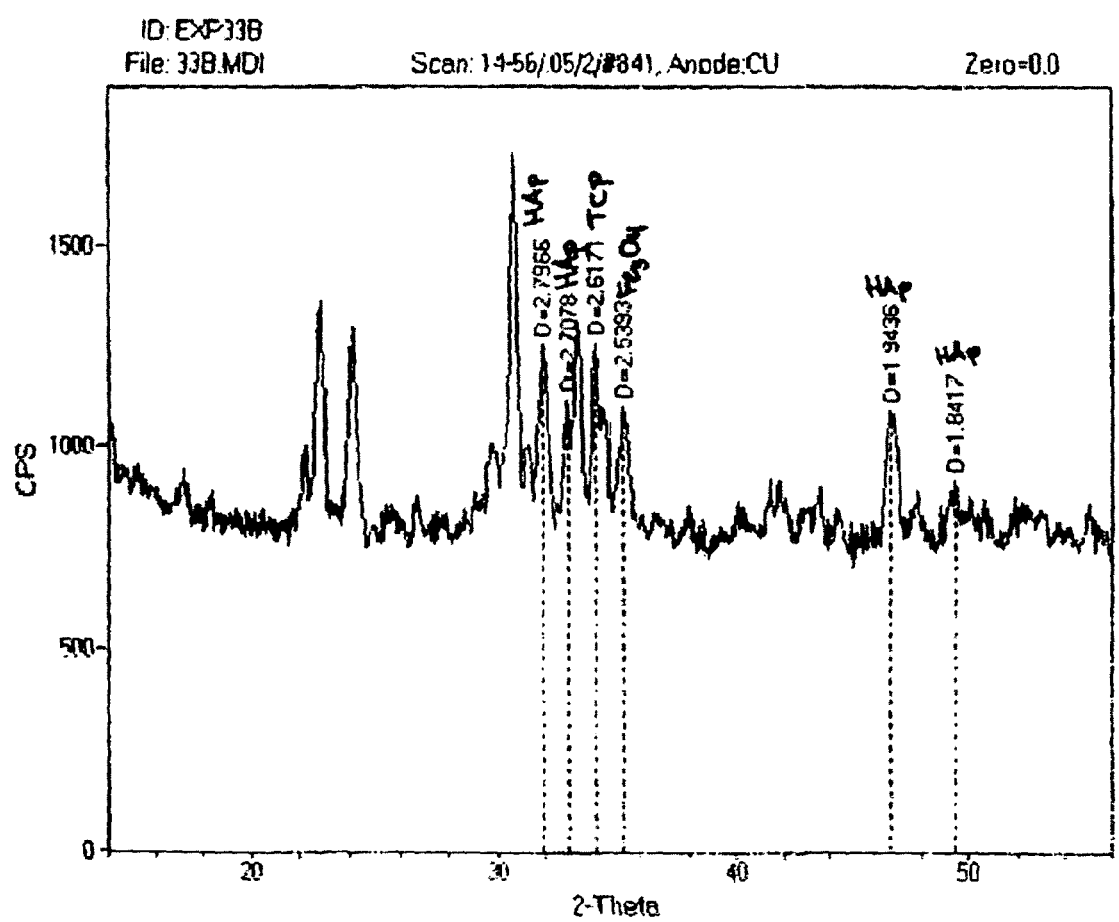
FIG. 17 shows x-ray diffraction data from a composition in accordance with this invention.

FIG. 17 shows X-ray diffraction results from one such sample. Other compositions of this invention show similar results, demonstrating reproducibility. With reference to FIG. 17, several hydroxyapatite peaks appear. Tricalcium phosphate and iron oxide peaks are also identified, indicating a primary phase of biphasic calcium phosphate with a relatively high hydroxyapatite/tricalcium phosphate ratio.

In certain embodiments, the method further comprises heat treating the cooled sample. In the examples examined, heat treating does not appear to show favorable results. In one embodiment, the step of heat treating included the steps of heating the sample to a temperature below the melting temperature, typically about 1000-1400 degrees Celsius, maintaining the temperature for about one half hour and furnace quenching. In another embodiment, the step of heat treating included the steps of heating to sample to about 25-50 degrees Celsius about the melting temperature, reducing the temperature below the melting temperature, maintaining the reduced temperature for about twenty minutes, and furnace quenching.

A section of the "as cast" rapidly cooled untreated sample is shown in FIG. 10, and a section of the heat treated portion of the sample is shown in FIG. 11. The absence of a noticeable change on inspection suggests that the prominent features of the structure are substantially developed in the product before heat treatment.

Figure 15:
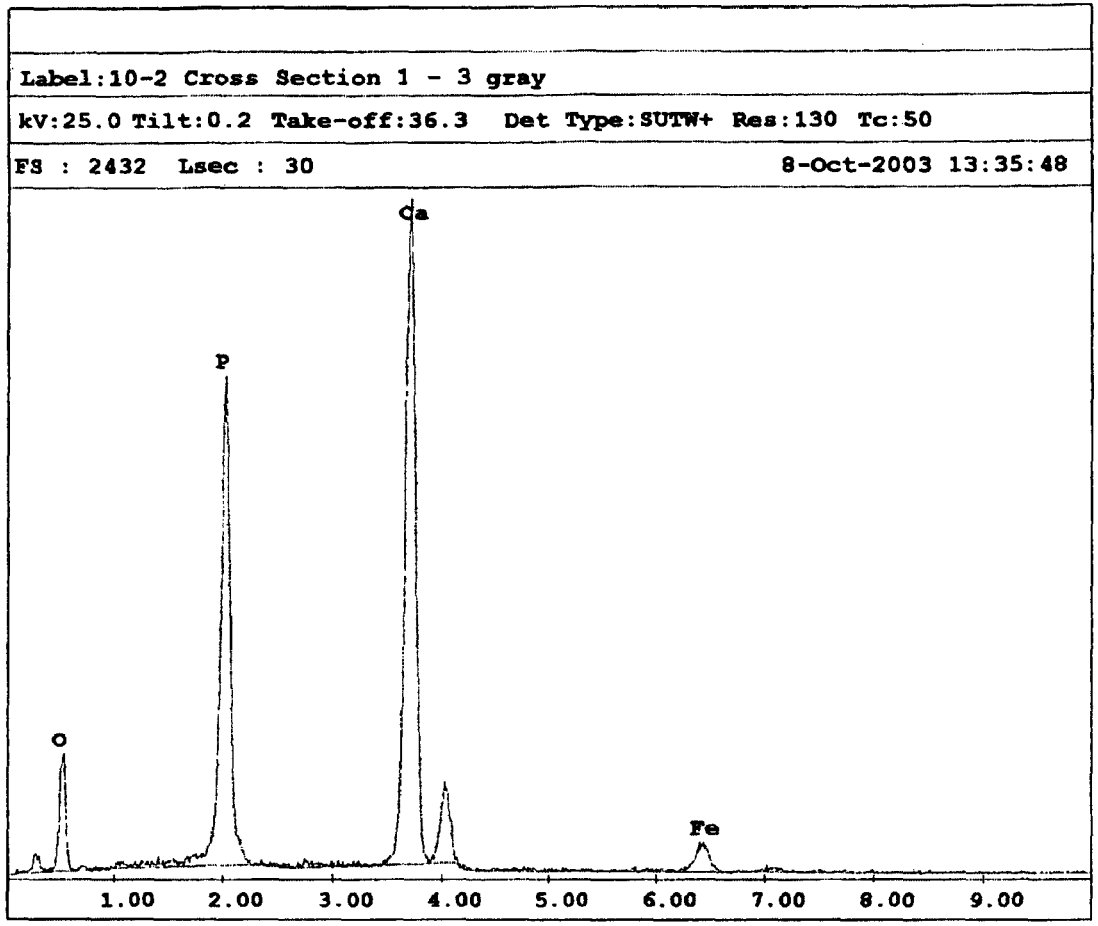
FIG. 15 is a graphical representation of the results of EDAX analysis of a calcium phosphate region of an sample section, showing relative amounts if Fe, Ca, P and O.

EDAX analysis was used to determine the Ca/P ratio. FIG. 15 is a graphical representation of the results of EDAX analysis of a calcium phosphate region of a sample section, showing relative amounts of Fe, Ca, P and O. As would be expected, the Ca/P ratios varied somewhat between areas on the same section, and varied by the composition of the product. For example, the Ca/P ratios of compositions 210G and 212I were 1.95 and 1.99. In other embodiments, the phosphate-rich regions of the non-heat treated samples typically had Ca/P ratios of approximately 1.5.

In general, the analysis of the formation of a composition comprising hydroxyapatite through spinodal decomposition showed that a spinodal region does occur in the CaO—$P_2O_5$—FeO ternary system and that it does generate microstructures typical of spinodal decomposition. It also appears that the phosphate floats, and that the phosphate regions have a Ca/P ratio typical of tricalcium phosphate. A porous biphasic calcium phosphate material can be created using this method, and in preferred embodiments, the second phase is primarily iron oxide.

In certain embodiments in which a second phase formed by spinodal decomposition is a transition metal oxide, removing 150 the second phase to provide a porous composition can be formed by preferential removal of the transition metal oxide by contacting the composition with a solution of a leaching agent. Preferably, the leaching agent is selected from the group consisting of an organic acid, a chelating agent, sequential use and/or a mixture thereof.

In selected, non-limiting embodiments, an iron oxide phase is removed by contacting a sample of the hydroxyapatite product with a solution of an organic acid, such as oxalic acid, or a chelating agent, such as a cyclic hydroxamic acid. Typically approximately 200 mL of leaching agent solution is used for a 2.5 g sample. The solution of the organic acid or chelating agent is placed inside a beaker and mixed using a magnetic stirrer. Heating simultaneously may also be required. The sample is treated for approximately 24 hours with the acid or about 1 week with the chelating agent.

Suitable organic acids include aliphatic dicarboxylic acids such as oxalic acid, malonic acid, succinic acid, glutaric acid, tartaric acid and D-glucaric acid. Other suitable organic acids include glycolic acid, gluconic acid, levulinic acid, acetic acid, lactic acid, citric acid and formic acid. A preferred organic acid is oxalic acid.

Chelating agents are often used at neutral or physiological pH, e.g., pH from about 7 to about 7.4. Often such chelating agents are acids, although they may be used in their acid form or as salts. In preferred embodiments, chelating agents are transition metal chelators, preferably compounds having a high binding constant for iron (III). Preferably the binding constant for iron ions is substantially greater than for calcium ions. In preferred embodiments, the chelating agents are cyclic hydroxamic acids (cyclic 1,4-benzoxazin-3-ones) and derivatives thereof, such as 2,4-dihydroxy-2H-1,4-benzoxazin-3(4H)-one (DIBOA), 2-4-dihydroxy-7-methoxy-1,4-benzoxazin-one (DIMBOA), acid and 3-amino-3,4-dihydro-1-hydroxycarbostyril (ADHC).

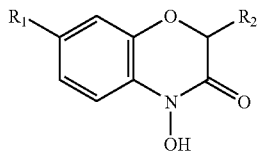

In general, cyclic hydroxamic acids can be represented by formula (I), where hydroxamic acid, R1,R2=H, DIBOA: R1=H, R2=OH; DIMBOA: R1=MeO, R2=OH. In preferred embodiments, the chelating agents have a binding constant for iron (III) of greater than $10^{15}$, preferably greater than $10^{20}$, and most preferably greater than $10^{26}$. Exemplary chelating agents include diethylenetriaminepentaacetic acid (DTPA), trans-1,2-diaminocyclohexane-N,N,N',N'-tetraacetic acid (CDTA), and triethylenetetraaminehexaacetic acid (TTHA).

In other embodiments, suitable transition metal chelators include iminodiacetate, tris(carboxymethyl)ethylenediamine (TED), pyridine-2,6-bis(thiocarboxylic acid), sodium 1-hydroxypyridine-2-thione, also known as sodium pyrithione (Pyr), 2,2'-bipyridine, deferoxamine mesylate, N,N,N',N'-tetrakis(2-pyridalmethyl)ethyl-enediamine (TPEN), 1,10-phenanthroline (Phen) and pyridoxal isonicotinoyl hydrazone (PIH).

In other embodiments, the transition metal chelators are tris[2-(2-hydroxy-3-(2-pyridinyl)-5-sulfobenzamido)ethyl] amine and derivatives (Baret, P., Trenpypols: a new water-soluble iron chelator (both FeIII and FeII) involving six-membered coordination rings, *Eur. J. Inorg. Chem.*, 2000, 1219-1227).

Catecholate chelating agents include cis-1,2-cyclohexylenedinitrilotetraacetate (CDTA), nitriloacetate (NTA), 4,5-dihydroxy-1,3-benzenesulfonic acid (TIRON), catechol, 4-nitrocatechol and enterobactin.

In one embodiment, hydroxylated aromatic compounds are used as chelating agents. Examples of hydroxylated aromatic chelating agents including hydroquinone, orcinol, resorcinol, trihydroxybenzene, salicylate, m-hydroxybenzoate, p-hydroxybenzoate, nitrilotriacetic acid and diethylenetriaminepentaacetate are disclosed in U.S. Pat. No. 6,623,211. In preferred embodiments, chelating agents for use in combination with iron as Fe(II) or Fe(III) as the transition metal include the hydroxybenzenes and the hydroxybenzoic acids, such as catechol (1,2 dihydroxybenzene) or gallic acid (3,4,5 trihydroxybenzoic acid). Gallic acid may be produced from plant tannins by standard well known chemical processes.

We claim:

1. A calcium phosphate spinodal decomposition product composition comprising a first phase comprising hydroxyapatite and tricalcium phosphate, and a second phase comprising a removable inorganic porogen, said phases interconnected and having continuous networks, said second phase interconnection having a substantially constant cross-sectional dimension.

2. The composition of claim 1 wherein said removable porogen is a transition metal oxide.

3. The composition of claim 2 wherein said transition metal oxide is selected from the group consisting of iron oxide, nickel oxide, cobalt oxide, manganese oxide and copper oxide.

4. The composition of claim 3 wherein said composition comprises an iron oxide content ranging from about 25 wt. % to about 65 wt. %.

5. The composition of claim 1 wherein each of said first and second phases have a cross-sectional dimension less than about 1.5 μm.

6. A calcium phosphate spinodal decomposition product of a molten mixture comprising iron oxide, calcium oxide and calcium phosphate, said product within the immiscibility region of a phase diagram of a $CaO$—$P_2O_5$—$FeO$ ternary system, said product comprising two interconnected phases having continuous networks.

7. The product of claim 6 comprising an iron oxide content ranging from about 25 wt. % to about 65 wt. %.

8. The product of claim 7 wherein said iron oxide content is about 40 wt. %.

9. The product of claim 6 comprising a Ca/P ratio between about 1.5 and about 2.0.

10. The product of claim 6 wherein each of said phases has a cross-sectional dimension less than about 1.5 μm.

11. A method of using a ternary system to prepare a biomimetic bone material, said method comprising:
providing a mixture of a transition metal oxide, calcium oxide and calcium phosphate components, each said component in an amount sufficient to provide a spinodal decomposition product within the immiscibility region of a phase diagram of a $CaO$—$P_2O_5$—$MO$ ternary system, where MO is selected from the group consisting of transition metal oxides;
heating said mixture over a temperature range and a time sufficient for spinodal decomposition of said mixture, said spinodal decomposition product comprising two interconnected phases having continuous networks; and
removing said MO component from said spinodal decomposition product, to provide a biomimetic bone material.

12. The method of claim 11 wherein said mixture is melted, and cooled at a rate sufficient to affect product microstructure.

13. The method of claim 12 wherein at least one of the amount of said MO and said rate of cooling affects the porosity of said biomimetic bone material.

14. The method of claim 11 wherein said removal comprises contacting said MO component with at least one of an acid and a chelating agent.

15. The method of claim 11 wherein said biomimetic bone material is sterilized.

16. A composition comprising a calcium phosphate spinodal decomposition product comprising a first phase comprising hydroxyapatite and tricalcium phosphate, and a second phase comprising a removable inorganic porogen, said phases interconnected and having continuous networks, said porogen at least partially removed to provide said composition a matrix of interconnected pores.

17. The composition of claim 16 wherein said matrix has a porosity ranging from about 30% to about 60%.

18. The composition of claim 17 wherein said pore size ranges from about 3 µm to about 700 µm.

19. The composition of claim 18 wherein said porosity ranges from about 55% to about 70%.

20. The composition of claim 19 wherein said matrix has a pore size chosen from a size ranging from about 500 µm to about 600 µm, a size ranging from about 190 µm to about 230 µm, and a size ranging from about 3 µm to about 30 µm.

21. The composition of claim 20 wherein said pores are of a dimension chosen from the pore dimension of a cancellous bone and the pore dimension of a cortical bone.

* * * * *